(12) United States Patent
Bandman et al.

(10) Patent No.: US 6,627,605 B1
(45) Date of Patent: Sep. 30, 2003

(54) HUMAN PROTEINASE MOLECULES

(75) Inventors: Olga Bandman, Mountain View, CA (US); Neil C. Corley, Mountain View, CA (US); Karl J. Guegler, Menlo Park, CA (US); Mariah R. Baughn, San Jose, CA (US)

(73) Assignee: Incyte Corporation, Palo Alto, CA (US)

( * ) Notice: Subject to any disclaimer, the term of this patent is extended or adjusted under 35 U.S.C. 154(b) by 40 days.

(21) Appl. No.: 09/802,633

(22) Filed: Mar. 8, 2001

Related U.S. Application Data

(62) Division of application No. 09/032,523, filed on Feb. 27, 1998, now Pat. No. 6,232,454.

(51) Int. Cl.$^7$ ............................................. A61K 38/00
(52) U.S. Cl. ........................... 514/12; 530/350; 435/7.1
(58) Field of Search ........................... 530/350; 514/12; 435/7.1, 174

(56) References Cited

U.S. PATENT DOCUMENTS 5,622,967 A   4/1997   Dolle et al.

FOREIGN PATENT DOCUMENTS

| WO | 94/21817 | 9/1994 |
| WO | 95/33060 | 12/1995 |

OTHER PUBLICATIONS

Beynon, R.J. and J.S. Bond (1994) *Proteolytic enzymes—a practical approach*, Oxford University Press, New York, NY pp. 1–5.

von Heijne, G. "A new method for predicting signal sequence cleavage sites", *Nuc. Acid. Res.*, 14:4683–4690 (1986).

Zunino, S.J. et al., "RNKP–1, A Novel Natural Killer–Associated Serine Protease Gene Cloned From RNK–16 Cytotoxic Lymphocytes", *J. Immunol.*, 144:2001–2009 (1990).

Sayers, T.J. et al., "Purification and Cloning of a Novel Serine Protease, RNK–Tryp–2, from the Granules of a Rat NK Cell Leukemia", *J. Immunol.*, 152:2289–2297 (1994).

Keyszer, G.M. et al., "Comparative Analysis of Cathepsin L, Cathepsin D, and Collagenase Messenger RNA Expression in Synovial Tissues of Patients With Rheumatoid Arthritis and Osteoarthritis, by in Situ Hybridization", *Arthritis Rheum.*, 38:976–984 (1995).

Chambers, A.F. and A.B. Tuck, "Ras–Responsive Genes and Tumor Metastasis", *Crit. Rev. Oncog.*, 4:95–114 (1993).

Mignatti, P., "Tumor Invasion through the Human Amniotic Membrane: Requirement for a Proteinase Cascade"*Cell*, 47:487–498 (1986).

Murphy, G. et al., "The Regulation of Connective Tissue Metalloproteinases by Natural Inhibitors", *Agents Actions Suppl.*, 35:69–76 (1991).

Calkins, C.C. and B.F. Sloane, "Mammalian Cysteine Protease Inhibitors: Biochemical Properties and Possible Roles in Tumor Progression", *Biol. Biochem. Hoppe Seyler*, 376:71–80 (1995).

Sakihama, T. et al., (Direct Submission), GenBank Sequence Database (Accession M11778), National Center for Biotechnology Information, National Library of Medicine, Bethesda. Maryland, 20894, (GI 164402; GI 164403) 1988.

Sakihama, T. et al., "A putative CA$^+$–binding protein: Structure of the light subunit of porcine calpain elucidated by molecular cloning and protein sequence analysis", *Proc. Natl. Acad. Sci. USA*, 82:6075–6079 (1985) (GI 164403).

Hirahara, I. et al., (Direct Submission), GenBank Sequence Database (Accession AB008548), National Center for Biotechnology Information, National Library of Medicine, Bethesda, Maryland, 20894, (GI 2589008; GI 2589009) (1997).

Azuma, T. et al., (Direct Submission), GenBank Sequence Database (Accession J05036), National Center for Biotechnology Information, National Library of Medicine, Bethesda, Maryland, 20894, (GI 181193: GI 181194) (1994).

Azuma, T. et al., "Human Gastric Cathepsin E", *J. Biol. Chem.*, 264:16748–16753 (1989) (GI 181194).

Beynon, R.J. and J.S. Bond (supra) pp. 25–55 1994.

Hillier et al., Database EST, Accession No. W07748, 1996.

Myers, Database Genembl, Accession No. G27716, 1996.

Myers, Database Genembl, Accession No. D24942 1996.

*Primary Examiner*—Sheela Huff
(74) *Attorney, Agent, or Firm*—Incyte Corporation

(57) ABSTRACT

The invention provides human proteinase molecules, the polynucleotides which encode them, and methods for their use. The invention also provides expression vectors, host cells, antibodies, agonists, and antagonists. The invention further provides methods for diagnosing or treating disorders associated with expression of HPRM.

8 Claims, 15 Drawing Sheets

FIGURE 1A

```
       9              18             27             36             45             54
TTT TTT CAT    ACC ATC TCT    AAG ATT GCT    GCC GCA TTT    GCT TGT TAA    ACT GAA AGC 63             72             81             90             99             108
ATG TTT CTT    GCA AAG GCT    CTA TTG GAA    GGA GCA GAT    CGA GGT CTT    GGA GAA GCT
 M   F   L      A   K   A      L   L   E      G   A   D      R   G   L      G   E   A 117            126            135            144            153            162
CTT GGA CTC    TTT GGA GGT    CAG AGA GGA    AGA GAA GGA    GGA GGA AGA    GGA AGA AAT
 L   G   L      F   G   G      Q   R   G      R   E   G      G   G   R      G   R   N 171            180            189            198            207            216
ATT GGG ATA    GTT GGA GGA    ATT GTG AAT    TTT ATC AGT    GAG GCT GCA    GCA GCA GCT
 I   G   I      V   G   G      I   V   N      F   I   S      E   A   A      A   A   A 225            234            243            252            261            270
CAG TAT CCA    CCG GAA CCA    CCT CCC CCC    ACT CAG CAG    CAT TTC ACC    AGT GTG GAG GCC
 Q   Y   P      P   E   P      P   P   P      T   Q   Q      H   F   T      S   V   E   A 279            288            297            306            315            324
TCA GAA GAG    GAA GAA GTT    AGG CGA TTT    CGG CAA CAA    TTT ACA CAG    CAG CTG GCT GGA
 S   E   E      E   E   V      R   R   F      R   Q   Q      F   T   Q      Q   L   A   G 333            342            351            360            369            378
CCA GAC ATG    GAG GTG GGT    GCC ACT GAT    CTG ATG AAT    ATT CTC AAC    AAA GTC CTT
 P   D   M      E   V   G      A   T   D      L   M   N      I   L   N      K   V   L
```

```
      387         396         405         414         423         432
TCT AAG CAC AAA GAT CTT AAG ACT GAC GGT TTT AGT CTT GAC ACC TGC CGG AGC
 S   K   H   K   D   L   K   T   D   G   F   S   L   D   T   C   R   S 441         450         459         468         477         486
ATT GTG TCT GTC ATG GAC AGT GAC ACG ACT GGT AAG CTG GGC TTT GAA GAA TTT
 I   V   S   V   M   D   S   D   T   T   G   K   L   G   F   E   E   F 495         504         513         522         531         540
AAG TAT CTG TGG AAC ATC AAG AAA TGG CAG TCT GTT TAT AAG CAG TAT GAC
 K   Y   L   W   N   I   K   K   W   Q   S   V   Y   K   Q   Y   D 549         558         567         576         585         594
AGG GAC CAT TCT CAG CTA TCT CTG GGA AGT CTG CAG CGG GGA GCT CTG CAG GCC
 R   D   H   S   Q   L   S   L   G   S   L   Q   R   G   A   L   Q   A 603         612         621         630         639         648
GCA GGC TTC CAG AAT GAA CAA CTT TAC CAA ATG ATT GTC CGC CGG TAT GCT
 A   G   F   Q   N   E   Q   L   Y   Q   M   I   V   R   R   Y   A 657         666         675         684         693         702
AAT GAA GAT GGA GAT ATG GAT TTT AAC AAT TTC ATC AGC TGC TTG GTC CGC CTG
 N   E   D   G   D   M   D   F   N   N   F   I   S   C   L   V   R   L 711         720         729         738         747         756
GAT GCC ATG TTT CGT GCC TTC AAG TCT CTG GAT AGA GAT AGA GAT GGC CTG ATT
 D   A   M   F   R   A   F   K   S   L   D   R   D   R   D   G   L   I
```

FIGURE 1B

```
                765            774            783            792            801            810
       CAA GTG TCT ATC AAA GAG TGG CTG CAG TTG ACC ATG TAT TCC TGA AGT GGG AAC
        Q   V   S   I   K   E   W   L   Q   L   T   M   Y   S 819            828            837            846            855            864
       TGA GAA GTC AAG ATC CTC CCT GGA GGA CAG GAC TGA AAA CCT TGC CAA GCT GTA 873            882            891            900            909            918
       CAC AGT TGC TGA TAC CCT GTG CAA CAG CTC TCA TTT CCT GGC AAG CTC TTT CAC 927            936            945            954            963            972
       AAC CCT ACA TAT TTC TGA TCA TGT GCT GCC TTT CCT TAC TGC TGA ATT AAA ACA GAT 981            990            999
       ATT TCA CGA AAA AAA AAA AAA AAA AAA AAA A 3'
```

FIGURE 1C

```
5' CGC TGT CGG TGC GGC GGC GCG CGT GGT GCA AAC CCG AGC GTC TAC GCT GCC          54

9       18      27      36      45      54

ATG AGG GGC GCG AAC GCC TGG GCG CCA CTC TGC CTG CTG CTG GCT GCC ACC          108
 M   R   G   A   N   A   W   A   P   L   C   L   L   L   A   A   T
    63      72      81      90      99     108

CAG CTC TCG CGG CAG TCC CAG AGA CCT GTT TTC ACA GGT GGC GCC GCC ATT          162
 Q   L   S   R   Q   S   Q   E   R   P   V   F   T   G   G   A   I
   117     126     135     144     153     162

CTT ACT GGA GAG TCT GGA TTT ATT GGC AGT GAA GGT TTT CCT GGA GTG TAC CCT      216
 L   T   G   E   S   G   F   I   G   S   E   G   F   P   G   V   Y   P
   171     180     189     198     207     216

CCA AAT AGC AAA TGT ACT TGG AAA ATC ACA GTT CCC GAA GGA AAA GTA GTC GTT      270
 P   N   S   K   C   T   W   K   I   T   V   P   E   G   K   V   V
   225     234     243     252     261     270

CTC AAT TTC CGA TTC ATA GAC CTC GAG AGT GAC AAC CTG TGC CGC TAT GAC TTT      324
 L   N   F   R   F   I   D   L   E   S   D   N   L   C   R   Y   D   F
   279     288     297     306     315     324

GTG GAT GTG TAC AAT GGC CAT GCC AAT GGC CAG CGC ATT GGC CGC TTC TGT GGC      378
 V   D   V   Y   N   G   H   A   N   G   Q   R   I   G   R   F   C   G
   333     342     351     360     369     378
```

FIGURE 2A

```
        387         396         405         414         423         432
ACT TTC CGG CCT GGA GCC CTT GTG TCC AGT GGC AAC AAG ATG ATG GTG CAG ATG
 T   F   R   P   G   A   L   V   S   S   G   N   K   M   M   V   Q   M 441         450         459         468         477         486
ATT TTT GAT GCC AAC ACA GCT GGC AAT GGC TTC ATG GCC ATG TTC TCC GCT GCT
 I   F   D   A   N   T   A   G   N   G   F   M   A   M   F   S   A   A 495         504         513         522         531         540
GAA AAC GAA AGA GGG GAT CAG TAT TGT GGA CTC CTT GAC AGA CCT TCC
 E   N   E   R   G   D   Q   Y   C   G   L   L   D   R   P   S 549         558         567         576         585         594
GGC TCT TTT AAA ACC CCC AAC TGG CCA GAC CGG GAT TAC CCT GCA GGA GTC ACT
 G   S   F   K   T   P   N   W   P   D   R   D   Y   P   A   G   V   T 603         612         621         630         639         648
TGT GTG TGG CAC ATT GTA GCC CCA AAG AAT CAG CTT ATA GAA TTA AAG TTT GAG
 C   V   W   H   I   V   A   P   K   N   Q   L   I   E   L   K   F   E 657         666         675         684         693         702
AAG TTT GAT GTG GAG CGA GAT AAC TAC TGC CGA TAT GAT TAT GTG GCT GTG TTT
 K   F   D   V   E   R   D   N   Y   C   R   Y   D   Y   V   A   V   F 711         720         729         738         747         756
AAT GGC GGG GAA GTC AAC GAT GCT AGA AGA ATT GGA AAG TAT TGT GGT GAT AGT
 N   G   G   E   V   N   D   A   R   R   I   G   K   Y   C   G   D   S
```

FIGURE 2B

```
                765              774              783              792              801              810
CCA CCT GCG CCA ATT GTG TCT GAG AGA AAT GAA CTT CTT ATT CAG TTT TTA TCA
 P   P   A   P   I   V   S   E   R   N   E   L   L   I   Q   F   L   S 819              828              837              846              855              864
GAC TTA AGT TTA ACT GCA GAT GGG TTT ATT GGT CAC TAC ATA TTC AGG CCA AAA
 D   L   S   L   T   A   D   G   F   I   G   H   Y   I   F   R   P   K 873              882              891              900              909              918
AAA CTG CCT ACA ACT GAA CAG CCT GTC ACC ACA TTC CCT GTA ACC ACG
 K   L   P   T   T   E   Q   P   V   T   T   F   P   V   T   T 927              936              945              954              963              972
GGT TTA AAA CCC ACC GTG GCC TTG TGT CAA CAA AAG TGT AGA CGG ACG GGG ACT
 G   L   K   P   T   V   A   L   C   Q   Q   K   C   R   R   T   G   T 981              990              999             1008             1017             1026
CTG GAG GGC AAT TAT TGT TCA AGT GAC TTT GTA TTA GCC GGC ACT GTT ATC ACA
 L   E   G   N   Y   C   S   S   D   F   V   L   A   G   T   V   I   T 1035             1044             1053             1062             1071             1080
ACC ATC ACT CGC GAT GGG AGT TTG CAC GCC ACA GTC TCG ATC ATC AAC ATC TAC
 T   I   T   R   D   G   S   L   H   A   T   V   S   I   I   N   I   Y 1089             1098             1107             1116             1125             1134
AAA GAG GGA AAT TTG GCG ATT CAG CAG GCG CAG GGC AAG AAC ATG AGT GCC AGG CTG
 K   E   G   N   L   A   I   Q   Q   A   Q   G   K   N   M   S   A   R   L
```

FIGURE 2C

```
     1143           1152           1161           1170           1179           1188
ACT GTC GTC TGC AAG CAG TGC CCT CTC CTC AGA AGA GGT CTA AAT TAC ATT ATT
 T   V   V   C   K   Q   C   P   L   L   R   R   G   L   N   Y   I   I 1197           1206           1215           1224           1233           1242
ATG GGC CAA GTA GGT GAA GAT GGG CGA GGC AAA ATC ATG CCA AAC AGC TTT ATC
 M   G   Q   V   G   E   D   G   R   G   K   I   M   P   N   S   F   I 1251           1260           1269           1278           1287           1296
ATG ATG TTC AAG ACC AAG AAT CAG AAG CTC CTG GAT GCC TTA AAA AAT AAG CAA
 M   M   F   K   T   K   N   Q   K   L   L   D   A   L   K   N   K   Q 1305           1314           1323           1332           1341           1350
TGT TAA CAG TGA ACT GTG TCC ATT TAA GCT GTA TTC TGC CAT TGC CTT TGA AAG
 C 1359           1368           1377           1386           1395           1404
ATC TAT GTT CTC TCA GTA GAA AAA ATA CTT ATA AAA TTA CAT ATT CTG AAA 1413           1422           1431           1440           1449           1458
GAG GAT TCC GAA AGA TGG GAC TGG TTG ACT CTT CAC ATG ATG GAG GTA TGA GGC 1467           1476           1485           1494           1503           1512
CTC CGA GAT AGC TGA GGG AAG TTC TTT GCC TGT CAG AGG AGC AGC TAT CTG
```

FIGURE 2D

```
         1521            1530            1539           1548            1557          1566
ATT GGA AAC CTG CCG ACT TAG TGC GGT GAT AGG AAG CTA AAA GTG TCA AGC GTT 1575            1584            1593           1602            1611          1620
GAC AGC TTG GAA GCG TTT ATT TAT ACA TCT CTG TAA AAG GAT ATT TTA GAA TTG 1629            1638            1647           1656            1665          1674
AGT TGT GTG AAG ATG TCA AAA AAA GAT TTT AGA AGT GCA ATA TTT ATA GTG TTA 1683            1692            1701           1710            1719          1728
TTT GTT TCA CCT TCA AGC CTT TGC CCT GAG GTG TTA CAA TCT TGT CTT GCG TTT 1737            1746            1755           1764            1773          1782
TCT AAA TCA ATG CTT AAT AAA ATA TTT TTA AAG GAA AAA AAA AAA AAA AAA AAA 1791            1800
AAA AAA AAA AAA AAA CGA AT 3'
```

FIGURE 2E

```
                                          11              20              29              38              47              56
5'CG GAG GGG GCA AGG GAG AAG CTG CTG GGA CTC GTC GGA CTC ACA ATG AAA ACG CTC CTT CTT
                                                                     M   K   T   L   L   L 65              74              83              92             101             110
TTG CTG CTG GTG CTC CTG GAG CTG CTG GGA GAG GCC CAA GGA TCC CTT CAC AGG GTG
 L   L   L   V   L   L   E   L   L   G   E   A   Q   G   S   L   H   R   V 119             128             137             146             155             164
CCC CTC AGG AGG CAT CCG TCC CTC AAG AAG AAG CTG CGG GCA AGC CAG CTC
 P   L   R   R   H   P   S   L   K   K   K   L   R   A   S   Q   L 173             182             191             200             209             218
TCT GAG TTC TGG AAA TCC CAT AAT TTG GAC ATG ATC CAG TTC ACC GAG TCC TGC
 S   E   F   W   K   S   H   N   L   D   M   I   Q   F   T   E   S   C 227             236             245             254             263             272
TCA ATG GAC CAG AGT GCC AAG GAA CCC CTC ATC AAC TAC TTG GAT ATG GAA TAC
 S   M   D   Q   S   A   K   E   P   L   I   N   Y   L   D   M   E   Y 281             290             299             308             317             326
TTC ACT ATC TCC ATT GGC TCC CCA CCA CAG AAC TTC GTC ATC TTC GAC
 F   T   I   S   I   G   S   P   P   Q   N   F   V   I   F   D 335             344             353             362             371             380
ACT GGC TCC TCC AAC CTC TGG GTC CCC TCT GTG TAC TGC ACT AGC CCA GCC TGC
 T   G   S   S   N   L   W   V   P   S   V   Y   C   T   S   P   A   C

FIGURE3A
```

```
389                398                407                416                425                434
AAG ACG CAC  AGC AGG TTC  CAG CCT TCC  CAG TCC AGC  ACA TAC AGC  CAG CCA GGT
 K   T   H    S   R   F    Q   P   S    Q   S   S    T   Y   S    Q   P   G 443                452                461                470                479                488
CAA TCT TTC  TCC ATT CAG  TAT GGA ACC  GGG AGC TTG  TCC GGG ATC  ATT GGA GCC
 Q   S   F    S   I   Q    Y   G   T    G   S   L    S   G   I    I   G   A 497                506                515                524                533                542
GAC CAA GTC  TCT GTG GAA  GGA CTA ACC  GTT GTT GGC  CAG CAG TTT  GGA GAA AGT
 D   Q   V    S   V   E    G   L   T    V   V   G    Q   Q   F    G   E   S 551                560                569                578                587                596
GTC ACA GAG  CCA GGC CAG  ACC TTT GTG  GAT GCA GAG  TTT GAT GGA  ATT CTG GGC
 V   T   E    P   G   Q    T   F   V    D   A   E    F   D   G    I   L   G 605                614                623                632                641                650
CTG GGA TAC  CCC TCC TTG  GCT GTG GAC  TTG CCG ATG  TTT TCT GTC  TAC CCA GTA
 L   G   Y    P   S   L    A   V   D    L   P   M    F   S   V    Y   P   V 659                668                677                686                695                704
ATG GCT CAG  AAC CTG GGA  AGC GAG CCG  ATG TTT TCT  GTC TAC ATG  AGC AGT AAC
 M   A   Q    N   L   G    S   E   P    M   F   S    V   Y   M    S   S   N 713                722                731                740                749                758
CCA GAA GGT  GGT GCC GGG  AGC GAG CTG  ATT TTT GGA  GGC TAC GAC  CAC TCC CAT
 P   E   G    G   A   G    S   E   L    I   F   G    G   Y   D    H   S   H
```

FIGURE 3B

```
      767             776         785         794         803         812
TTC TCT GGG AGC CTG AAT TGG GTC CCA GTC ACC AAG CAA GCT TAC TGG CAG ATT
 F   S   G   S   L   N   W   V   P   V   T   K   Q   A   Y   W   Q   I 821             830         839         848         857         866
GCA CTG GAT AAC TAT GCT GTG GAG TGT GCC AAC CTT AAC GTC ATG CCG GAT GTC
 A   L   D   N   Y   A   V   E   C   A   N   L   N   V   M   P   D   V 875             884         893         902         911         920
ACC TTC ACC ATT AAC GGA GTC CCC TAT ACC CTC AGC CCA ACT GCC TAC ACC CTA
 T   F   T   I   N   G   V   P   Y   T   L   S   P   T   A   Y   T   L 929             938         947         956         965         974
CTG GAC TTC GTG GAT GGA ATG CAG TTC TGC AGC AGT GGC TTT CAA GGA CTT GAC
 L   D   F   V   D   G   M   Q   F   C   S   S   G   F   Q   G   L   D 983             992         1001        1010        1019        1028
ATC CAC CCT CCA GCT GGG CCC CTC TGG ATC CTG GGG GAT GTC TTC ATT CGA CAG
 I   H   P   P   A   G   P   L   W   I   L   G   D   V   F   I   R   Q 1037            1046        1055        1064        1073        1082
TTT TAC TCA GTC TTT GAC CGT GGG AAT AAC CGT GTG GGA CTG GCC CCA GCA GTC
 F   Y   S   V   F   D   R   G   N   N   R   V   G   L   A   P   A   V 1091            1100        1109        1118        1127        1136
CCC TAA GGA GGG GCC TTG TGT CTG TGC CTG CCT GTC TGA CAG ACC TTG AAT ATG
 P

FIGURE3C
```

```
1145        1154        1163        1172        1181        1190
TTA GGC TGG GGC ATT CTT TAC ACC TAC AAA AAG TTA TTT TCC AGA GAA TGT AGC
     1199        1208        1217        1226        1235        1244
TGT TTC CAG GGT TGC AAC TTG AAT TAA GAC CAA ACA GAA CAT GAG AAT ACA CAC
     1253        1262        1271        1280        1289        1298
ACA CAC CAT ATA CAC ACA CAC ACA CTT CAC ACA TAC ACA CCA CTC CCA CCA
     1307        1316        1325        1334        1343        1352
CCG TCA TGA TGG AGG AAT TAC GTT ATA CAT TCA TAT TTT GTA TTG ATT TTT GAT
     1361        1370        1379        1388        1397        1406
TAT GAA AAT CAA AAA TTT TCA CAT TTG ATT ATG AAA ATC TCC AAA CAT ATG CAC
     1415        1424        1433        1442        1451        1460
AAG CAG AGA TCA TGG TAT AAT AAA TCC CTT TGC AAC TCC ACT CAG CCC TGA CAA
     1469        1478        1487        1496        1505        1514
CCC ATC CAC ACA CGG CCA GGC CTG TTT ATC TAC ACT GCT GCC CAC TCC TCT CTC
     1523        1532        1541        1550        1559        1568
CAG CTC CAC ATG CTG TAC CTG GAT CAT TCT GAA GCA AAT TCC GAG CAT TAC ATC
     1577        1586        1595        1604        1613        1622
ATT TTG TCC ATA AAT ATT TCT AAC ATC CTT AAA TAT ACA ATC GGA ATT CAA GCA
```

FIGURE 3D

```
     1631      1640      1649      1658      1667      1676
TCT CCC ATT GTC CCA CAA ATG TTT GGC TGT TTT TGT AGT TGG ATT GTT TGT ATT
     1685      1694      1703      1712      1721      1730
AGG ATT CAA GCA AGG CCC ATA TAT TGC ATT TAT TTG AAA TGT CTG TAA GTC TCT
     1739      1748      1757      1766      1775      1784
TTC CAT CTA CAG AGT TTA GCA CAT TTG AAC GTT GCT GGT TGA AAT CCC GAG GTG
     1793      1802      1811      1820      1829      1838
TCA TTT GAC ATG GTT CTC TGA ACT TAT CTT TCC TAT AAA ATG GTA GTT AGA TCT
     1847      1856      1865      1874      1883      1892
GGA GGT CTG ATT TTG TGG CAA AAA TAC TTC CTA GGT GCT GGG TAC TTC TTG
     1901      1910      1919      1928      1937      1946
TTG CAT CCT GTC AGG AGG CAG ATA ATG CTG GTG CCT CTC TAT TGG TAA TGT TAA
     1955      1964      1973      1982      1991      2000
GAC TGC TGG GTG GGT TTG GAG TTC TTG GCT TTA ATC ATT CAT TAC AAA GTT CAG
     2009      2018      2027      2036      2045      2054
CAT TTT AAA AAA AAA AAA GGA AAA AAA AAG GAA AAA AAA GAG AAA AAA GAA
     2063      2072
AAA AAA AAG GAA AGA GGG G 3'
```

FIGURE 3E

| | | |
|---|---|---|
| 1 | MFLAKALLEGADRG------LGEALG | 456855 |
| 1 | MFLVNSFLKGGGGGGGLGGGLGNVLG | g164403 |
| 21 | GLFGGGQRREGGGRNIGG-----IV | 456855 |
| 31 | GLISGAGGGGGGGGGTAMRIL | g164403 |
| 42 | GGIVNFISEAAAAQYTPEPPPTQQHFTSVE | 456855 |
| 61 | GGVISAISEAAA-QYNPEPPPRTHYSNIE | g164403 |
| 72 | ASESEEVRRFRQQFTQLAGPDMEVGATDLM | 456855 |
| 90 | ANESEEVRQFRRLFAQLAGDDMEVSATELM | g164403 |
| 102 | NILNKVLSKHKDLKTDGFSLDTCRSIVSVM | 456855 |
| 120 | NILNKVVTRHPDLKTDGFIDTCRSMVAVM | g164403 |

HUMAN PROTEINASE MOLECULES

This application is a divisional of U.S. Ser. No. 09/032,523, filed Feb. 27, 1998 now U.S. Pat. No. 6,232,454.

FIELD OF THE INVENTION

This invention relates to nucleic acid and amino acid sequences of human proteinase molecules and to the use of these sequences in the diagnosis and treatment of cancer and immune disorders.

BACKGROUND OF THE INVENTION

Proteolytic processing is an essential component of normal cell growth, differentiation, remodeling, and homeostasis. The cleavage of peptide bonds within cells is necessary for the maturation of precursor proteins to their active form, the removal of signal sequences from targeted proteins, the degradation of incorrectly folded proteins, and the controlled turnover of peptides within the cell.

Proteases participate in apoptosis, antigen presentation, inflammation, tissue remodeling during embryonic development, wound healing, and normal growth. They are necessary components of bacterial, parasitic, and viral invasion and replication within a host. Four principal categories of mammalian proteases have been identified based on active site structure, mechanism of action, and overall three-dimensional structure (Beynon and Bond (1994) *Proteolytic Enzymes: A Practical Approach*, Oxford University Press, New York N.Y., pp. 1–5).

The serine proteases (SPs) are a large family of proteolytic enzymes that include the digestive enzymes, trypsin and chymotrypsin; components of the complement cascade and of the blood-clotting cascade; and enzymes that control the degradation and turnover of macromolecules of the extracellular matrix. SPs are so named because of the presence of a serine residue found in the active catalytic site for protein cleavage. The active site of all SP is composed of a triad of residues including the aforementioned serine, an aspartate, and a histidine residue. SPs have a wide range of substrate specificities and can be subdivided into subfamilies on the basis of these specificities. The main sub-families are trypases which cleave after arginine or lysine; aspases which cleave after aspartate; chymases which cleave after phenylalanine or leucine; metases which cleavage after methionine; and serases which cleave after serine.

The SPs are secretory proteins containing N-terminal signal peptides which export the immature protein across the endoplasmic reticulum prior to cleavage (von Heijne (1986) Nuc Acid Res 14:5683–5690). Differences in these signal sequences provide one means of distinguishing individual SPs. Some SPs, particularly the digestive enzymes, exist as inactive precursors or preproenzymes and contain a leader or activation peptide on the C-terminal side of the signal peptide. This activation peptide may be 2–12 amino acids in length and extend from the cleavage site of the signal peptide to the N-terminus of the active, mature protein. Cleavage of this sequence activates the enzyme. This sequence varies in different SPs according to the biochemical pathway and/or its substrate (Zunino et al. (1990) J Immunol 144:2001–2009; Sayers et al. (1994) J Immunol 152:2289–2297).

Cysteine proteases are involved in diverse cellular processes ranging from the processing of precursor proteins to intracellular degradation. Mammalian cysteine proteases include lysosomal cathepsins and cytosolic calcium activated proteases, cilpains. Cysteine proteases are produced by monocytes, macrophages and other cells of the immune system which migrate to sites of inflammation and in their protective role secrete various molecules to repair damaged tissue. These cells may overproduce the same molecules and cause tissue destruction in certain disorders. In autoimmune diseases such as rheumatoid arthritis, the secretion of the cysteine protease, cathepsin C, degrades collagen, laminin, elastin and other structural proteins found in the extracellular matrix of bones. The cathepsin family of lysosomal proteases includes the cysteine proteases; cathepsins B, H, K, L, O2, and S; and the aspartyl proteases; cathepsins D and E. Various members of this endosomal protease family are differentially expressed. Some, such as cathepsin D, have a ubiquitous tissue distribution while others, such as cathepsin L, are found only in monocytes, macrophages, and other cells of the immune system.

Abnormal regulation and expression of cathepsins has been implicated in various inflammatory disease states. In cells isolated from inflamed synovia, the mRNA for stromelysin, cytokines, TIMP-1, cathepsin, gelatinase, and other molecules is preferentially expressed. Expression of cathepsins L and D is elevated in synovial tissues from patients with rheumatoid arthritis and osteoarthritis. Cathepsin L expression may also contribute to the influx of mononuclear cells which exacerbate the destruction of the rheumatoid synovium (Keyszer (1995) Arthritis Rheum 38:976–984). The increased expression and differential regulation of the cathepsins is linked to the metastatic potential of a variety of cancers and may be of therapeutic and prognostic interest (Chambers et al. (1993) Crit Rev Oncog 4:95–114).

Cysteine proteases are characterized by a catalytic domain containing a triad of amino acid residues similar to that found in serine proteases. A cysteine replaces the active serine residue. Catalysis proceeds via a thiol ester intermediate and is facilitated by the side chains of the adjacent histidine and aspartate residues.

Aspartic proteases include bacterial penicillopepsin, mammalian pepsin, renin, chymosin, cathepsins D and E, and certain fungal proteases. The characteristic active site residues of aspartic proteases are a pair of aspartic acid residues, such as asp33 and asp213 in penicillopepsin. Aspartic proteases are also called acid proteases because the optimum pH for activity is between 2 and 3. In this pH range, only one of the aspartate residues is ionized. A potent inhibitor of aspartic proteases is the hexapeptide, pepstatin, which in the transition state resembles a normal substrate of the enzyme.

Metalloproteases use zinc as an active site component and are most notably represented in mammals by the exopeptidases, carboxypeptidase A and B, and the matrix metalloproteases, collagenase, gelatinase, and stromelysin. Carboxypeptidases A and B are exopeptidases of similar structure and active sites. Carboxypeptidase A, like chymotrypsin, prefers hydrophobic C-terminal aromatic and aliphatic side chains, whereas carboxypeptidase B is directed toward basic arginine and lysine residues. The matrix-metalloproteases are secreted by connective tissue cells and play an important role in the maintenance and function of the basement membrane and extracellular matrix. A naturally occurring inhibitor of metalloproteases, tissue inhibitor of metalloproteases (TIMP), has been shown to prevent the invasion of tumor cells through basement membrane, in vitro, indicating the importance of these enzymes in cell invasion processes such as tumor metastasis and the inflammatory response (Mignatti et al. (1986) Cell 47:487–498).

Protease inhibitors play a major role in the regulation of the activity and effect of proteases. They have been shown to control pathogenesis in animal models of proteolytic disorders (Murphy (1991) Agents Actions Suppl 35:69–76). In particular, low levels of the cystatins, low molecular weight inhibitors of the cysteine proteases, seem to be correlated with malignant progression of tumors (Calkins et al. (1995) Biol Biochem Hoppe Seyler 376:71–80). The balance between levels of cysteine proteases and their inhibitors is also significant in the development of disorders. Specifically, increases in cysteine protease levels, when accompanied by reductions in inhibitor activity, are correlated with increased malignant properties of tumor cells and the pathology of arthritis and immunological diseases in humans.

The discovery of new human proteinase molecules and the polynucleotides encoding them satisfies a need in the art by providing new compositions which are useful in the diagnosis and treatment of cancer and immune disorders.

SUMMARY OF THE INVENTION

The invention features purified polypeptides, human proteinase molecules, referred to collectively as "HPRM" and individually as "HPRM-1"; "HPRM-2", and "HPRM-3". In one embodiment, the purified polypeptide, HPRM, comprises an amino acid sequence selected from the group consisting of SEQ ID NO:1, SEQ ID NO:2, and SEQ ID NO:3, and fragments of SEQ ID NOs: 1–3.

The invention includes a purified variant having at least 90% amino acid identity to the amino acid sequences of SEQ ID NOs: 1–3 or fragments thereof.

The invention provides an isolated and purified polynucleotide encoding the polypeptide comprising an amino acid sequence selected from the group consisting of SEQ ID NOs:1–3 and fragments thereof. The invention also includes an isolated variant having at least 90% sequence identity to the polynucleotide encoding the polypeptide comprising an amino acid sequence selected from the group consisting of SEQ ID NOs:1–3 and fragments thereof.

The invention also provides an isolated polynucleotide comprising a nucleic acid sequence selected from the group consisting of SEQ ID NO:4, SEQ ID.NO:5, and SEQ ID NO:6 and fragments and complements of SEQ ID NOs:4–6. The invention includes a variant having at least 90% sequence identity to the polynucleotide selected from the group consisting of SEQ ID NOs:4–6 and complements and fragments thereof.

The invention further provides an expression vector containing at least a fragment of the polynucleotide encoding the polypeptide comprising an amino acid sequence selected from the group consisting of SEQ ID NOs:1–3 and fragments thereof. In another aspect, the expression vector is contained within a host cell. The invention still further provides a the method for using a polynulceotide to produce a polypeptide comprising culturing the host cell containing an expression vector containing at least a fragment of a polynucleotide encoding the polypeptide under conditions for the expression of the polypeptide and recovering the polypeptide from the host cell culture.

The invention yet still further provides a method for using a polynucleotide to detect a nucleic acid encoding a polypeptide having the amino acid sequence of SEQ ID NOs:1–3 in a sample comprising hybridizing the polynucleotide or the complement thereof to at least one nucleic acid in the sample, thereby forming a hybridization complex and detecting the hybridization complex, wherein the presence of the hybridization complex indicates the expression of the nucleic acid in the sample. In one aspect, the nucleic acids of the sample are amplified prior to hybridization.

The invention additionally provides a method of using a polynucleotide to screen a plurality of molecules to identify a molecule which specifically binds the polynucleotide comprising combining the polynucleotide with the plurality of molecules under conditions to allow specific binding and detecting specific binding, thereby identifying a molecule which specifically binds the polynucleotide. In one aspect, the molecule is selected from DNA molecules, RNA molecules, peptide nucleic acids, artificial chromosome constructions, peptides, and proteins.

The method provides purified polypeptides comprising an amino acid sequence selected from SEQ ID NO:1, SEQ ID NO:2, SEQ ID NO:3, and fragments thereof. In one aspect, a biologically active fragment of the polypeptide is selected from residues D132–F144 of SEQ ID NO:1, residues C34–C415 of SEQ ID NO:2 and residues V93–V104 of SEQ ID NO:3.

The invention also provides a method for using a polypeptide to screen a plurality of molecules to identify a molecule which specifically binds the polypeptide comprising combining the polypeptide with the plurality of molecules under conditions to allow specific binding and detecting specific binding, thereby identifying a molecule which specifically binds the polypeptide. In one aspect, the molecules are selected from agonists, antagonists, antibodies, DNA molecules, RNA molecules, peptide nucleic acids, immunoglobulins, inhibitors, drug compounds, peptides, and pharmaceutical agents.

The invention further provides a method of using a polypeptide to purify a molecule which specifically binds the polypeptide from a sample comprising combining the polypeptide with a sample under conditions to allow specific binding, recovering the bound polypeptide, and separating the molecule from the polypeptide, thereby obtaining the purified molecule.

The invention still further provides a method for using a polypeptide to produce an antibody, comprising immunizing an animal with the polypeptide under conditions to elicit an antibody response and isolating antibodies which bind specifically to the polypeptide.

The invention yet further provides a method for using a polypeptide to purify an antibody which specifically binds the polypeptide comprising combining the polypeptide with a plurality of antibodies under conditions allow specific binding, recovering the bound polypeptide, and separating the antibody from the polypeptide, thereby obtaining antibody which specifically binds the polypeptide. In one tin aspect, the antibodies are selected from polyclonal antibodies, monoclonal antibodies, chimeric antibodies, single chain antibodies; Fab fragments, Fv fragments, and F(ab')$_2$ fragments.

The invention additionally provides a purified antibody which specifically binds the polypeptide having the amino acid sequence selected from the group consisting of SEQ ID NOs:1–3 and fragments thereof.

The invention provides compositions comprising an isolated polynucleotide encoding a polypeptide having an amino acid sequence selected from the group consisting of SEQ ID NOs:1–3 and fragments thereof and reporter molecule or a purified polypeptide having an amino acid sequence selected from the group consisting of SEQ ID NOs:1–3 and fragments thereof and a pharmaceutical carrier.

The invention also provides a method for treating or preventing a cancer, the method comprising administering to a subject in need of such treatment an effective amount of an antagonist of the polypeptide having an amino acid sequence selected from the group consisting of SEQ ID NOs:1–3 and fragments thereof.

The invention further provides a method for treating or preventing an immune disorder, the method comprising administering to a subject in need of such treatment an effective amount of an antagonist of the polypeptide having an amino acid sequence selected from the group consisting of SEQ ID NOs:1–3 and fragments thereof.

BRIEF DESCRIPTION OF THE FIGURES

FIGS. 1A, 1B, and 1C show the amino acid sequence (SEQ ID NO:1) and nucleic acid sequence (SEQ ID NO:4) of HPRM-1. The alignment was produced using MACD-NASIS PRO software (Hitachi Software Engineering, San Bruno Calif.).

FIGS. 2A, 2B, 2C, 2D, and 2E show the amino acid sequence (SEQ ID NO:2) and nucleic acid sequence (SEQ ID NO:5) of HPRM-2. The alignment was produced using MACDNASIS PRO software.

FIGS. 3A, 3B, 3C, 3D, and 3E show the amino acid sequence (SEQ ID NO:3) and nucleic acid sequence (SEQ ID NO:6) of HPRM-3. The alignment was produced using MACDNASIS PRO software.

FIGS. 4A and 4B show the amino acid sequence alignments between HPRM-1 (456885; SEQ ID NO:1), and a pig calpain I light subunit (GI 164403; SEQ ID NO:7), produced using the multisequence alignment program of LASER-GENE software (DNASTAR, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HPRM" refers to the amino acid sequences of purified HPRM obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to HPRM, increases or prolongs the duration of the effect of HPRM. Agonists may include proteins, nucleic acids, carbohydrates, or any other molecules which bind to and modulate the effect of HPRM.

"Altered" nucleic acid sequences encoding HPRM include those sequences with deletions, insertions, or substitutions of different nucleotides, resulting in a polynucleotide the same HPRM or a polypeptide with at least one functional characteristic of HPRM. Included within this definition are polymorphisms which may or may not be readily detectable using a particular oligonucleotide probe of the polynucleotide encoding HPRM, and improper or unexpected hybridization to alleles, with a locus other than the normal chromosomal locus for the polynucleotide sequence encoding HPRM. The encoded protein may also be "altered" and may contain deletions, insertions, or substitutions of amino acid residues which produce a silent change and result in a functionally equivalent HPRM. Deliberate amino acid substitutions may be made on the basis of similarity in polarity, charge, solubility, hydrophobicity, hydrophilicity, and/or the amphipathic nature of the residues, as long as the biological or immunological activity of HPRM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HPRM which are preferably about 5 to about 15 amino acids in length and which retain some biological activity or immunological activity of HPRM. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art (Dieffenbach and Dveksler (1995) *PCR Primer, a Laboratory Manual*, Cold Spring Harbor Press, Plainview N.Y., pp. 1–5).

The term "antagonist" refers to a molecule which, when bound to HPRM, decreases the amount or the duration of the effect of the biological or immunological activity of HPRM. Antagonists may include proteins, nucleic acids, carbohydrates, antibodies, or any other molecules which decrease the effect of HPRM.

The term "antibody" refers to intact molecules as well as to fragments thereof, such as Fa, F(ab')$_2$, and Fv fragments, which are capable of binding the epitopic determinant. Antibodies that bind HPRM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule, an epitope, that makes contact with a particular antibody. When a protein or a fragment of a protein is used to immunize a host animal, numerous regions of the protein may induce the production of antibodies which bind specifically to antigenic determinants, given regions or three-dimensional structures on the protein. An antigenic determinant may compete with the intact antigen, the immunogen used to elicit the immune response, for binding to an antibody.

The term "biologically active" refers to a protein having structural, regulatory, or biochemical functions of a naturally occurring molecule. Likewise, "immunologically active" refers to the capability of the natural, recombinant, or synthetic HPRM, or of any oligopeptide thereof, to induce a specific immune response in appropriate animals or cells and to bind with specific antibodies.

The terms "complementary" or "complementarity" refer to the natural binding of polynucleotides under permissive salt and temperature conditions by base pairing. For example, the sequence "A-G-T" binds to the complementary sequence "T-C-A". The degree of complementarity between nucleic acid strands has significant effects on the efficiency and strength of the hybridization. This is of particular importance in amplification reactions, which depend upon binding between nucleic acids strands, and in the design and use of peptide nucleic acid (PNA) molecules. The inhibition of hybridization of a completely complementary sequence to the target sequence may be examined using a hybridization assay (Southern or northern blot, solution hybridization, and the like) under conditions of reduced stringency.

A "composition comprising a given polynucleotide" or a "composition comprising a given polypeptide" refer broadly to any composition containing the given polynucleotide or polypeptide and at least one other molecule. The other molecule specifically encompasses labeling moeities, reporter molecules, and pharmaceutical excipients and carriers.

"Consensus sequence" refers to a nucleic acid sequence which has been resequenced to resolve uncalled bases, extended using XL-PCR kit (Applied Biosystems (ABI), Foster City Calif.) in the 5' and/or the 3' direction, and resequenced, or which has been assembled from the overlapping sequences of more than one Incyte Clone using a computer program for fragment assembly, such as the GEL-VIEW Fragment Assembly system (Genetics Computer Group, Madison Wis.). Some sequences have been both extended and assembled to produce the consensus sequence.

The term "correlates with expression of a polyniicleotide" indicates that the detection of the presence of nucleic acids, the same or related to a polynucleotide encoding HPRM, by northern analysis is indicative of the presence of nucleic acids encoding BPRM in a sample, and thereby correlates with expression of the transcript from the polynucleotide encoding HPRM.

A "deletion" refers to a change in the amino acid or nucleotide sequence that results in the absence of one or more amino acid residues or nucleotides.

The term "derivative" refers to the chemical modification of HPRM, of a polynucleotide encoding HPRM, or of a polynucleotide complementary to a polynucleotide encoding HPRM. Chemical modifications of a polynucleotide can include, for example, replacement of hydrogen by an alkyl, acyl, or amino group. A derivative polynucleotide encodes a polypeptide which retains at least one biological or immunological function of the natural polypeptide. A derivative polypeptide is one modified by glycosylation, pegylation, or any similar process that retains at least one biological or immunological function of the natural polypeptide.

The term "homology" refers to a degree of similarity or "identity". "Percent identity" refers to the percentage of sequence identity found in a comparison of two or more amino acid or nucleic acid sequences. Percent identity can be determined electronically, e.g., by using the multisequence alignment program of LASERGENE software (DNASTAR). This program can create alignments between two or more sequences according to selected method, e.g., the clustal method (Higgins and Sharp (1988) Gene 73:237–244). The clustal algorithm groups sequences into clusters by examining the distances between all pairs. The clusters are aligned pairwise, and then, in groups. The percentage identity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage identity. Percent identity between nucleic acid sequences can also be counted or calculated by methods known in the art, e.g., the Jotun Hein method (Hein (1990) Methods Enzymol 183:626–645).

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution or formed between one nucleic acid sequence present in solution and another nucleic acid sequence immobilized on a substrate.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The phrases "nucleic acid" or "nucleic acid sequence" refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked" refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. Oligonucleotide is equivalent to the terms "amplimer", "primer", and "oligomer".

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation; they may be pegylated to extend their lifespan in the cell (Nielsen et al. (1993) Anticancer Drug Des 8:53–63).

The term "sample" is used in its broadest sense. A biological sample suspected of containing nucleic acids encoding HPRM, or fragments thereof, or HPRM itself, may comprise a bodily fluid; an extract from cell media, a cell, chromosome, organelle, or membrane isolated from a cell; a cell; genomic DNA, RNA, or cDNA, in solution or bound to a solid support; a tissue; a tissue print; etc.

"Specific binding" refers to a specific interaction between a nucleotide or protein and molecules with which it interacts. These molecules include, but are not limited to, DNA molecules, RNA molecules, peptide nucleic acids, artificial chromosome constructions, peptides, proteins, agonists, antibodies, antagonists, immunoglobulins, inhibitors, drug compounds, peptides, and pharmaceutical agents. The interaction between the polynucleotide or polypeptide and the bound molecule is dependent upon the presence of a particular structure of the polynucleotide or protein recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotide sequences and the claimed polynucleotide sequences. Suitably stringent conditions can be defined by, for example, the concentrations of salt or fornamide in the prehybridization and hybridization solutions, or by the hybridization temperature, and are well known in the art. In particular, stringency can be increased by reducing the concentration of salt, increasing the concentration of formamide, or raising the hybridization temperature.

The term "purified" refers to nucleic acid or amino acid sequences that are removed from their natural environment or cell culture media and are isolated or separated, and are at least about 60% free, preferably about 75% free, and most preferably about 90% free from other components with which they are associated.

"Specific binding" refers to a specific interaction between a nucleotide or protein and molecules with which it interacts. These molecules include, but are not limited to, DNA molecules, RNA molecules, peptide nucleic acids, artificial chromosome constructions, peptides, proteins, agonists, antibodies, antagonists, immunoglobulins, inhibitors, drug compounds, peptides, and pharmaceutical agents. The interaction between the polynucleotide or polypeptide and the bound molecule is dependent upon the presence of a particular structure of the polynucleotide or protein recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

"Substrate" refers to any solid support including, but not limited to, membranes, filters, chips, slides, wafers, fibers, magnetic or nonmagnetic beads, gels, capillaries or other tubing, plates, polymers, and microparticles with a variety of surface forms including wells, trenches, pins, channels and pores to which cells or their nucleic acids have been attached.

A "variant" of HPRM refers to a nucleotide or amino acid sequence that is altered by one or more nucleotides or amino acids. The variant may have "conservative" changes wherein the substituted moiety has similar structural or chemical properties (e.g., a purine is substituted for a purine or a leucine is replaced with an isoleucine). Analogous minor variations may also include at least one amino acid deletion or insertion, or both. Guidance in determining which amino acid residues may be substituted, inserted, or deleted without abolishing biological or immunological activity may be found using computer programs well known in the art such as LASERGENE software (DNASTAR).

The Invention

The invention is based on the discovery of new human proteinase molecules (HPRM), the polynucleotides encoding HPRM and the use of these compositions for the diagnosis and treatment of cancer and immune disorders.

Nucleic acids encoding the HPRM-1 of the present invention were first identified in Incyte Clone 456855 from the keratinocyte cDNA library (KERANOT01) using a computer search for amino acid sequence alignments. A consensus sequence, SEQ ID NO:4, was derived from the following overlapping and/or extended nucleic acid sequences: Incyte Clones 456855 (KERANOT01) and 3363138 (PROSBPT02).

In one embodiment, the invention encompasses a polypeptide comprising the amino acid sequence of SEQ ID NO:1 as shown in FIGS. 2A–2E. UPRM-1 is 248 amino acids in length and contains potential phosphorylation sites for casein kinase II at T68, S73, S129, and S237, and for protein kinase C at T123, T136, and S237, and for tyrosine kinase at Y146. HPRM-1 also contains a potential EF-hand calcium-binding domain between residues D132 and F144. As shown in FIGS. 4A–4B, HPRM-1 has chemical and structural homology with the calcium-binding, calpain I light subunit from pig (GI 164403; SEQ ID NO:7). In particular, HPRM-1 and the pig calpain subunit share 65% homology. The pig calpain subunit shares the EF-hand calcium-binding domain, and the potential phosphorylation sites found at residues T68, T123, and Y146 in HPRM-1. A fragment of SEQ ID NO:4 from about nucleotide 145 to about nucleotide 193 is useful for hybridization. Northern analysis shows the expression of this sequence in skin, neonatal keratinocytes, and hyperplastic prostate cDNA libraries.

Nucleic acids encoding the HPRM-2 of the present invention were first identified in Incyte Clone 947429 from the atrium tissue cDNA library (RATRNOT02) using a computer search for amino acid sequence alignments. A consensus sequence, SEQ ID NO:5, was derived from the following overlapping and/or extended nucleic acid sequences: Incyte Clones 947429 (RATRNOT02), 870803 and 877928 (LUNGAST01), 907964 (COLNNOTO9), and 2632243 (COLNTUT15).

In another embodiment, the invention encompasses a polypeptide comprising the amino acid sequence of SEQ ID NO:2, as shown in FIGS. 2A–2E. HPRM-2 is 415 amino acids in length and has a potential signal peptide sequence between residues M1 and Q23. A potential N-glycosylation site is found at residue N355, and potential phosphorylation sites are found for casein kinase II at T64, S142, and T274, for protein kinase C at T60, T109, S164, S241, and S357, and for tyrosine kinase at Y207. Cysteine residues, representing potential intramolecular disulfide bridging sites are found at residues C34, C59, C86, C107, C154, C 181, C208, C231, C297, C312, C364, and C415. HPRM-2 has chemical and homology with mouse procollagen C-proteinase enhancer (GI 2589009;SEQ ID NO:8). In particular, HPRM-2 and mouse procollagen C-proteinase enhancer share 42% homology, the phosphorylation sites at T64, T109, and S357, and the twelve cysteine residues found in HPRM-2. A fragment of SEQ ID NO:5 from about nucleotide 405 to about nucleotide 513 is useful for hybridization. Northern analysis shows the expression of this sequence in various libraries, at least 45% of which are immortalized or cancerous and at least 31% of which involve immune response. Of particular note is the expression of HPRM in tumors of the testes, lung, heart, colon, and bladder, and in inflammatory conditions including rheumatoid arthritis, asthma, and Crohn's disease.

Nucleic acids encoding the HPRM-3 of the present invention were first identified in Incyte Clone 1516165 from the pancreatic tumor cDNA library (PANCTUT01) using a computer search for amino acid sequence alignments. A consensus sequence, SEQ ID NO:6, was derived from the following overlapping and/or extended nucleic acid sequences: Incyte Clones 1516165 (PANCTUT01), 1360069 (LUNGNOT12), 794210 (OVARNOT03), and shotgun sequences SAWA02729, SAWA00677, SAWA01399, and SAWA00459.

In another embodiment, the invention encompasses a polypeptide comprising the amino acid sequence of SEQ ID NO:3, as shown in FIGS. 3A–3E. HPRM-3 is 349 amino acids in length and has a potential signal peptide sequence from residue M1 to A17, a potential N-glycosylation site at residue N90, and potential phosphorylation sites for casein kinase II at S65, S168, T175, S221, T293, and and for protein kinase C at S31 and S65. HPRM-3 also contains a potential eukaryotic aspartyl protease active site signature sequence between residues V93 and V104, in which D96 is the catalytic site. HPRM-3 has chemical and structural homology with human cathepsin E precursor (GI 181194; SEQ ID NO:9). In particular, HPRM-3 and the human cathepsin E precursor share 88% homology. HPRM-3 is an apparent splice variant of the human cathepsin E precursor in which the sequence of the latter molecule between residues I263 and E309 has been deleted. The fragment of SEQ ID NO:6 from about nucleotide 807 to about nucleotide 857, which encompasses this deletion, is useful for hybridization.

Northern analysis shows the expression of this sequence in various libraries, at least 61% of which are immortalized or cancerous and at least 32% of which involve immune response. Of particular note is the expression of HPRM-3 in tumors of the ovaries, pancreas, testes, and lung, and in inflammatory conditions including asthma, lymphocytic thyroiditis, and inflamed adenoids.

The invention also encompasses HPRM variants. A preferred HPRM variant is one which has at least about 80%, more preferably at least about 90%, and most preferably at least about 95% amino acid sequence identity to the HPRM amino acid sequence, and which contains at least one functional or structural characteristic of HPRM.

The invention also encompasses polynucleotides which encode HPRM. In a particular embodiment, the invention encompasses a polynucleotide sequence comprising the sequence of SEQ ID NO:4, as shown in FIGS. 1A–1C, which encodes an HPRM. In a further embodiment, the invention encompasses the polynucleotide sequence comprising the sequence of SEQ ID NO:5, as shown in FIGS. 2A–2E. In a further embodiment, the invention encompasses the polynucleotide sequence comprising the sequence of SEQ ID NO:6, as shown in FIGS. 3A–3E.

The invention also encompasses a variant of a polynucleotide sequence encoding HPRM. In particular, such a variant polynucleotide sequence will have at least about 80%, more preferably at least about 90%, and most preferably at least about 95% polynucleotide sequence identity to the polynucleotide sequence encoding HPRM. A particular aspect of the invention encompasses a variant of SEQ ID NO:4 which has at least about 80%, more preferably at least about 90%, and most preferably at least about 95% polynucleotide sequence identity to SEQ ID NO:4. The invention further encompasses a polynucleotide variant of SEQ ID NO:5 having at least about 80%, more preferably at least about 90%, and most preferably at least about 95% polynucleotide sequence identity to SEQ ID NO:5. The invention further encompasses a polynucleotide variant of SEQ ID NO:6 having at least about 80%, more preferably at least about 90%, and most preferably at least about 95% polynucleotide sequence identity to SEQ ID NO:6. Any one of the polynucleotide variants described above can encode an amino acid sequence which contains at least one functional or structural characteristic of HPRM.

It will be appreciated by those skilled in the art that as a result of the degeneracy of the genetic code, a multitude of polynucleotide sequences encoding HPRM, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HPRM, and all such variations are to be considered as being specifically disclosed.

Although nucleotide sequences which encode HPRM and its variants are preferably capable of hybridizing to the nucleotide sequence of the naturally occurring HPRM under appropriately selected conditions of stringency, it may be advantageous to produce nucleotide sequences encoding HPRM or its derivatives possessing a different codon usage. Codons may be selected to increase the rate at which expression of the peptide occurs in a particular prokaryotic or eukaryotic host in accordance with the frequency with which particular codons are utilized by the host. Other reasons for altering the nucleotide sequence encoding HPRM and its derivatives without altering the encoded amino acid sequences include the production of RNA transcripts having more desirable properties, such as a greater half-life, than transcripts produced from the naturally occurring sequence.

The invention also encompasses production of DNA sequences which encode HPRM and HPRM derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HPRM or any fragment thereof.

Also encompassed by the invention are polynucleotide sequences that are capable of hybridizing to the claimed polynucleotide sequences, and, in particular, to those shown in SEQ ID NOs:4–6 or fragments thereof under various conditions of stringency (Wahl and Berger (1987) Methods Enzymol 152:399–407; Kimmel (1987) Methods Enzymol 152:507–511).

Methods for DNA sequencing are well known and generally available in the art and may be used to practice any of the embodiments of the invention. The methods may employ such enzymes as the Klenow fragment of DNA polymerase I, SEQUENASE, Taq polymerase, thermostable T7 polymerase (Amersham Pharmacia Biotech (APB), Piscataway N.J.), or combinations of polymerases and proofreading exonucleases such as those found in the ELONGASE amplification system (Life Technologies, Rockville Md.). Preferably, the process is automated with machines such as the MICROLAB 2200 (Hamilton, Reno Nev.), DNA ENGINE thermal cycler (MJ Research, Waltham Mass.) and the CATALYST and 373 and 377 PRISM DNA sequencing systems (ABI).

The nucleic acid sequences encoding HPRM may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus (Sarkar (1993) PCR Methods Applic 2:318–322). In particular, genomic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al. (1988) Nucleic Acids Res 16:8186). The primers may be designed using commercially available software such as OLIGO software (Molecular Biology Insights, Cascade Colo.) or another appropriate program to be about 22 to 30 nucleotides in length, to have a GC content of about 50% or more, and to anneal to the target sequence at temperatures of about 68° C. to 72° C. The method uses several restriction enzymes to generate a fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA (Lagerstrom et al. (1991) PCR Methods Applic 1:111–119). In this method, multiple restriction enzyme digestions and ligations may be used to place an engineered double-stranded, sequence into an unknown fragment of the DNA molecule before performing PCR. Other methods which may be used to retrieve unknown sequences are known in the art (Parker et al. (1991) Nucleic Acids Res 19:3055–3060). Additionally, one may use PCR, nested primers, and PROMOTERFINDER libraries to walk genomic DNA (Clontech, Palo Alto Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR software, ABI), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HPRM may be used in recombinant DNA molecules.to direct expression of HPRM, or fragments or functional equivalents thereof, in appropriate host cells. Due to the inherent degeneracy of the genetic code, other DNA sequences which encode the same or a functionally equivalent amino acid sequence may be produced, and these sequences may be used to clone and express HPRM.

As will be understood by those of skill in the art, it may be advantageous to produce HPRM-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HPRM-encoding sequences for a variety of reasons including, but not limited to, alterations which modify the cloning, processing, and/or expression of the gene product.

DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HPRM may be ligated to a heterologous sequence to encode a fusion protein. For example, to screen peptide libraries for inhibitors of HPRM activity, it may be useful to encode a chimeric HPRM protein that can be recognized by a commercially available antibody. A fusion protein may also be engineered to contain a cleavage site located between the HPRM encoding sequence and the heterologous protein sequence, so that HPRM may be cleaved and purified away from the heterologous moiety.

In another embodiment, sequences encoding HPRM may be synthesized, in whole or in part, using chemical methods well known in the art (Caruthers et al. (1980) Nucleic Acids Symp Ser (7) 215–223; Horn et al. (1980) Nucleic Acids Symp Ser (7) 225–232). Alternatively, the protein itself may be produced using chemical methods to synthesize the amino acid sequence of HPRM, or a fragment thereof. For example, peptide synthesis can be performed using various solid-phase techniques (Roberge et al. (1995) Science 269:202–204). Automated synthesis may be achieved using the 431A peptide synthesizer (ABI). Additionally, the amino acid sequence of HPRM, or any part thereof, may be altered during direct synthesis and/or combined with sequences from other proteins, or any part thereof, to produce a variant polypeptide.

The peptide may be purified by preparative high performance liquid chromatography (Chiez and Regnier (1990) Methods Enzymol 182:392–421). The composition of the synthetic peptides may be confirmed by amino acid analysis or by sequencing (Creighton (1984) *Proteins, Structures and Molecular Properties*, W H Freeman, New York N.Y.).

In order to express a biologically active HPRM, the nucleotide sequences encoding HPRM or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HPRM and appropriate transcriptional and translational control elements. These methods include in vitro recombinant DNA techniques, synthetic techniques, and in vivo genetic recombination. (See, e.g., Sambrook et al. (1989) *Molecular Cloning, A Laboratory Manual*, Cold Spring Harbor Press, Plainview N.Y., ch. 4, 8, and 16–17; Ausubel et al. (1995, and periodic supplements) *Current Protocols in Molecular Biology*, John Wiley & Sons, New York N.Y., ch. 9, 13, and 16.)

A variety of expression vector/host systems may be utilized to contain and express sequences encoding HPRM. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HPRM which interact with host cellular proteins to carry out transcription and translation. Such elements may vary in their strength and specificity. Depending on the vector system and host utilized, any number of transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla Calif.) or PSPORT 1 plasmid (Life Technologies), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HPRM, vectors based on SV40 or EBV may be used with an appropriate selectable marker.

In bacterial systems, a number of expression vectors may be selected depending upon the use intended for HPRM. For example, when large quantities of HPRM are needed for the induction of antibodies, vectors which direct high level expression of fusion proteins that are readily purified may be used. Such vectors include, but are not limited to, multifunctional *E. coli* cloning and expression vectors such as BLUESCRIPT phagemid (Stratagene), in which the sequence encoding HPRM may be ligated into the vector in frame with sequences for the amino-terminal Met and the subsequent 7 residues of β-galactosidase so that a hybrid protein is produced, and pin vectors. (Van Heeke and Schuster (1989) J Biol Chem 264:5503–5509). PGEX vectors (APB) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used (Ausubel, supra; Grant et al. (1987) Methods Enzymol 153:516–544).

In cases where plant expression vectors are used, the expression of sequences encoding HPRM may be driven by any of a number of promoters. For example, viral promoters such as the 35S and 19S promoters of CaMV may be used alone or in combination with the omega leader sequence from TMV (Takamatsu (1987) EMBO J 6:307–311). Alternatively, plant promoters such as the small subunit of RUBISCO or heat shock promoters may be used (Coruzzi et al. (1984) EMBO J 3:1671–1680; Broglie et al. (1984) Science 224:838–843; and Winter et al. (1991) Results Probl Cell Differ 17:85–105). These constructs can be introduced into plant cells by direct DNA transformation or pathogen-mediated transfection. Such techniques are described in a number of generally available reviews (Hobbs or Murry (1992) In: *Yearbook of Science and Technology*, McGraw Hill, New York N.Y.; pp. 191–196).

An insect system may also be used to express HPRM. For example, in one such system, *Autographa californica* nuclear polyhedrosis virus (AcNPV) is used as a vector to express foreign genes in *Spodoptera frugiperda* cells or in Trichoplusia larvae. The sequences encoding HPRM may be cloned into a non-essential region of the virus, such as the polyhedrin gene, and placed under control of the polyhedrin promoter. Successful insertion of sequences encoding HPRM will render the polyhedrin gene inactive and produce recombinant virus lacking coat protein. The recombinant viruses may then be used to infect, for example, *S. frugiperda* cells or Trichoplusia larvae in which HPRM may be expressed (Engelhard et al. (1994) Proc Nat Acad Sci 91:3224–3227).

In mammalian host cells, a number of viral-based expression systems may be utilized. In cases where an adenovirus is used as an expression vector, sequences encoding HPRM may be ligated into an adenovirus transcription/translation complex consisting of the late promoter and tripartite leader sequence. Insertion in a non-essential E1 or E3 region of the viral genome may be used to obtain a viable virus which is capable of expressing HPRM in infected host cells (Logan and Shenk (1984) Proc Natl Acad Sci 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HPRM. Such signals include the ATG initiation codon and adjacent sequences. In cases where sequences encoding HPRM and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used (Scharf et al. (1994) Results Probl Cell Differ 20:125–162).

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the ATCC (Bethesda Md.) and may be chosen to ensure the correct modification and processing of the foreign protein.

For long term, high yield production of recombinant proteins, stable expression is preferred. For example, cell lines capable of stably expressing HPRM can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk or apr cells, respectively (Wigler et al. (1977) Cell 11:223–232; Lowy et al. (1980) Cell 22:817–823). Also, antimetabolite, antibiotic, or herbicide resistance can be used as the basis for selection. For example, dhfr confers resistance to methotrexate; npt confers resistance to the aminoglycosides neomycin and G418; and als or pat confer resistance to chlorsulfuron and phosphinotricin acetyltransferase, respectively (Wigler et al. (1980) Proc Natl Acad Sci 77:3567–3570; Colbere-Garapin et al. (1981) J Mol Biol 150:1–14; and Murry, supra). Additional selectable genes have been described, e.g., trpB, which allows cells to utilize indole in place of tryptophan, or hisD, which allows cells to utilize histinol in place of histidine (Hartman and Mulligan (1988) Proc Natl Acad Sci 85:8047–8051). Visible markers such as anthocyanins, β glucuronidase and its substrate GUS, luciferase and its substrate luciferin may be used. Green fluorescent proteins (GFP; Clontech) can also be used. These markers can be used not only to identify transformants, but also to quantify the amount of transient or stable protein expression attributable to a specific vector system (Rhodes et al. (1995) Methods Mol Biol 55:121–131).

Although the presence/absence of marker gene expression suggests that the gene of interest is also present, the presence and expression of the gene may need to be confirmed. For example, if the sequence encoding HPRM is inserted within a marker gene sequence, transformed cells containing sequences encoding HPRM can be identified by the absence of marker gene function. Alternatively, a marker gene can be placed in tandem with a sequence encoding HPRM under the control of a single promoter. Expression of the marker gene in response to induction or selection usually indicates expression of the tandem gene as well.

Alternatively, host cells which contain the nucleic acid sequence encoding HPRM and express HPRM may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HPRM can be detected by DNA-DNA or DNA-RNA hybridization or amplification using probes or fragments or fragments of polynucleotides encoding HPRM. Nucleic acid amplification based assays involve the use of oligonucleotides or oligomers based on the sequences encoding HPRM to detect transformants containing DNA or RNA encoding HPRM.

A variety of protocols for detecting and measuring the expression of HPRM, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HPRM is preferred, but a competitive binding assay may be employed. These and other assays are well described in the art (Hampton et al. (1990) *Serological Methods, a Laboratory Manual*, APS Press, St Paul Minn., Section IV; Maddox et al. (1983) J Exp Med 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HPRM include oligolabeling, nick translation, end-labeling, or PCR amplification using a labeled nucleotide. Alternatively, the sequences encoding HPRM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits such as those provided by APB. Reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HPRM may be cultured under conditions for the expression and recovery of the protein from cell culture. The protein produced by a transformed cell may be secreted or contained intracellularly depending on the sequence and/or the vector used. As will be understood by those of skill in the art, expression vectors containing polynucleotides which encode HPRM may be designed to contain signal sequences which direct secretion of HPRM through a prokaryotic or eukaryotic cell membrane. Other constructions may be used to join sequences encoding HPRM to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex., Seattle, Wash.). The inclusion of cleavable linker sequences, such as those specific for Factor XA (APB) or enterokinase (Invitrogen, Carlsbad Calif.), between the purification domain and the HPRM encoding sequence may be used to facilitate purification. One such expression vector provides for expression of a fusion protein containing HPRM and a nucleic acid encoding 6 histidine residues preceding a thioredoxin or an enterokinase cleavage site. The histidine residues facilitate purification on immobilized metal ion affinity chromatography (Porath et al. (1992) Prot Exp Purif 3: 263–281). The enterokinase cleavage site provides a means for purifying HPRM from the fusion protein (Kroll et al. (1993) DNA Cell Biol 12:441453).

Fragments of HPRM may be produced not only by recombinant production, but also by direct peptide synthesis using solid-phase techniques (Creighton (1984) *Protein: Structures and Molecular Properties*, pp. 55–60, W H Freeman, New York N.Y.). Protein synthesis may be performed by manual techniques or by automation. Automated synthesis may be achieved, for example, using the 431A peptide synthesizer (ABI). Various fragments of HPRM may be synthesized separately and then combined to produce the full length molecule.

Therapeutics

Chemical and structural homology exists among HPRM and the calcium-binding, calpain I subunit from pig (GI 164403), a procollagen-C proteinase enhancer protein from mouse (GI 2589009), and an aspartic proteinase, cathepsin E, from human (GI 181194). In addition, HPRM is expressed in cancer and the immune response. Therefore, HPRM appears to play a role in cancer and immune disorders.

Therefore, in one embodiment, an antagonist of HPRM may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HPRM may be used directly as an antagonist or indirectly as a targeting or delivery mechanism for bringing a pharmaceutical agent to cells or tissue which express HPRM.

In another embodiment, a vector expressing the complement of the polynucleotide encoding HPRM may be administered to a subject to treat or prevent a cancer including, but not limited to, those described above.

In another embodiment, an antagonist of HPRM may be administered to a subject to treat or prevent an immune disorder. Such an immune disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dernmatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In an additional embodiment, a vector expressing the complement of the polynucleotide encoding HPRM may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment of the various disorders described above. Using this approach, one may be able to achieve therapeutic efficacy with lower dosages of each agent, thus reducing the potential for adverse side effects.

An antagonist of HPRM may be produced using methods which are generally known in the art. In particular, purified HPRM may be used to produce antibodies or to screen libraries of pharmaceutical agents to identify those which specifically bind HPRM. Antibodies to HPRM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies, those which inhibit dimer formation, are especially preferred for therapeutic use.

For the production of antibodies, various hosts including goats, rabbits, rats, mice, humans, and others may be immunized by injection with HPRM or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HPRM have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HPRM amino acids may be fused with those of another protein, such as KLH, and antibodies to the chimeric molecule may be produced.

Monoclonal antibodies to HPRM may be prepared using any technique which provides for the production of antibody molecules by continuous cell lines in culture. These include, but are not limited to, the hybridoma technique, the human B-cell hybridoma technique, and the EBV-hybridoma technique (Kohler et al. (1975) Nature 256:495497; Kozbor et al. (1985) J Inmunol Methods 81:31–42; Cote et al. (1983) Proc Natl Acad Sci 80:2026–2030; and Cole et al. (1984) Mol Cell Biol 62:109–120).

In addition, techniques developed for the production of "chimeric antibodies," such as the splicing of mouse antibody genes to human antibody genes to obtain a molecule with appropriate antigen specificity and biological activity, can be used (Morrison et al. (1984) Proc Natl Acad Sci 81:6851–6855; Neuberger et al. (1984) Nature 312:604–608; and Takeda et al. (1985) Nature 314:452–454). Alternatively, techniques described for the production of single chain antibodies may be adapted, using methods known in the art, to produce HPRM-specific single chain antibodies. Antibodies with related specificity, but of distinct idiotypic composition, may be generated by chain shuffling from random combinatorial immunoglobulin libraries (Burton (1991) Proc Nati Acad Sci 88:10134–10137).

Antibodies may also be produced by inducing in vivo, production in the lymphocyte population or by screening immunoglobulin libraries or panels of highly specific binding reagents as disclosed in the literature (Orlandi et al. (1989) Proc Natl Acad Sci 86: 3833–3837; Winter et al. (1991) Nature 349:293–299).

Antibody fragments which contain specific binding sites for HPRM may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 246:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPRM and its specific antibody. A two-site, monoclonal-based immunoassay utilizing monoclonal antibodies reactive to two non-interfering HPRM epitopes is preferred, but a competitive binding assay may also be employed (Maddox, supra.).

In another embodiment of the invention, the polynucleotides encoding HPRM, or any fragment or complement thereof, may be used for therapeutic purposes. In one aspect, the complement of the polynucleotide encoding HPRM may be used in situations in which it would be desirable to block the transcription of the mRNA. In particular, cells may be transformed with sequences complementary to polynucleotides encoding HPRM. Thus, complementary molecules or fragments may be used to modulate HPRM activity, or to achieve regulation of gene function. Such technology is now well known in the art, and sense or antisense oligonucleotides or larger fragments can be designed from various locations along the coding or control regions of sequences encoding HPRM.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HPRM (Sambrook, supra; Ausubel, supra).

Genes encoding HPRM can be turned off by tranisforming a cell or tissue with expression vectors which express high levels of a polynucleotide, or fragment thereof, encoding HPRM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HPRM. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee et al. (1994) In: Huber and Carr, *Molecular and Immunologic Approaches*, Futura Publishing, Mt. Kisco N.Y., pp. 163–177). A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HPRM.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HPRM. Such DNA sequences may be incorporated:into a wide variety of vectors with RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art (Goldman et al. (1997) Nature Biotechnol 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HPRM, antibodies to HPRM, and mimetics, agonists, antagonists, or inhibitors of HPRM. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate. Auxiliaries can be added, if desired.

Dragee cores may be used in conjunction with coatings, such as concentrated sugar solutions, which may also contain gum arabic, talc, polyvinylpyrrolidone, carbopol gel, polyethylene glycol, and/or titanium dioxide, lacquer solutions, and organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in liquids, such as fatty oils, liquid, or liquid polyethylene glycol with or without stabilizers.

Pharmaceutical formulations for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain stabilizers or agents to increase the solubility of the compounds and allow for the preparation of highly concentrated solutions.

For topical or nasal administration, penetrants appropriate to the particular barrier to be permeated are used in the formulation. Such penetrants.are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HPRM, such labeling would include amount, frequency, and method of administration.

Pharmaceutical compositions for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HPRM or fragments thereof, antibodies of HPRM, and agonists, antagonists or inhibitors of HPRM, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HPRM may be used for the diagnosis of disorders characterized by expression of HPRM, or in assays to monitor patients being treated with HPRM or agonists, antagonists, or inhibitors of HPRM. Antibodies useful for diagnostic purposes may be prepared in the same manner as described above for therapeutics. Diagnostic assays for HPRM include methods which utilize the antibody and a label to detect HPRM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HPRM, including ELISAs, RIAs, and FACS, are known in the art and provide a basis for diagnosing altered or abnormal levels of HPRM expression. Normal or standard values for HPRM expression are established by combining body fluids or cell extracts taken from normal mammalian subjects, preferably human, with antibody to HPRM under conditions for complex formation. The amount of standard complex formation may be quantitated by various methods, preferably by photometric means. Quantities of HPRM expressed in subject, control, and disease samples from biopsied tissues are compared with the standard values. Deviation between standard and subject values establishes the parameters for diagnosing disease.

In another embodiment of the invention, the polynucleotides encoding HPRM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HPRM may be correlated with disease. The diagnostic assay may be used to determine absence, presence, and excess expression of HPRM, and to monitor regulation of HPRM levels during therapeutic intervention.

In one aspect, hybridization with PCR probes which are capable of detecting polynucleotide sequences, including genomic sequences, encoding HPRM or closely related molecules may be used to identify nucleic acid sequences which encode HPRM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HPRM, alleles, or related sequences.

Probes may also be used for the detection of related sequences, and should preferably have at least 50% sequence identity to any of the HPRM encoding sequences. The hybridization probes of the subject invention may be DNA or RNA and may be derived from the sequences of SEQ ID NOs:4–6 or from genomic sequences including promoters, enhancers, and introns of the HPRM gene.

Means for producing specific hybridization probes for DNAs encoding HPRM include the cloning of polynucleotide sequences encoding HPRM or HPRM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via a vidin/biotin coupling systems, and the like.

Polynucleotide sequences encoding HPRM may be used for the diagnosis of a disorder associated with expression of HPRM. Examples of such a disorder include, but are not limited to, cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erytheinatosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HPRM may be used in Southern or northern analysis, dot blot, or other membrane-based technologies; in PCR technologies; in dipstick, pin, and ELISA assays; and in microarrays utilizing fluids or tissues from patients to detect altered HPRM expression. Such qualitative or quantitative methods are well known in the art.

In a particular aspect, the nucleotide sequences encoding HPRM may be useful in assays that detect the presence of associated disorders, particularly those mentioned above. The nucleotide sequences encoding HPRM may be labeled by standard methods and added to a fluid or tissue sample from a patient under conditions for the formation of hybridization complexes. After an incubation period, the sample is washed and the signal is quantitated and compared with a standard value. If the amount of signal in the patient sample is significantly altered in comparison to a control sample then the presence of altered levels of nucleotide sequences encoding HPRM in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HPRM, a normal or standard profile for expression is established. This may be accomplished by combining body fluids or cell extracts taken from normal subjects, either animal or human, with a sequence, or a fragment thereof, encoding HPRM, under conditions for hybridization or amplification. Standard hybridization may be quantified by comparing the values obtained from normal subjects with values from an experiment in which a known amount of a purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HPRM may involve the use of PCR. These oligomers may be chemically synthesized, generated enzymatically, or produced in vitro. Oligomers will preferably contain a fragment of a polynucleotide encoding HPRM, or a fragment of a polynucleotide complementary to the polynucleotide encoding HPRM, and will be employed under optimized conditions for identification of a specific gene or condition. Oligomers may also be employed under less stringent conditions for detection or quantitation of closely related DNA or RNA sequences.

Methods which may also be used to quantitate the expression of HPRM include radiolabeling or biotinylating nucleotides, coamplification of a control nucleic acid, and interpolating results from standard curves (Melby et al. (1993) J Inmuunol Methods 159:235–244; Duplaa et al. (1993) Anal Biochem 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art (Brennan, et al. (1995) U.S. Pat. No. 5,474,796; Schena et al. (1996) Proc Natl Acad Sci 93:10614–10619; Baldeschweileret al. (1995) PCT application WO95/251116; Shalon et al. (1995) PCT application WO95/35505; Heller et al. (1997) Proc Natl Acad Sci 94:2150–2155; and Heller et al. (1997) U.S. Pat. No. 5,605, 662).

In another embodiment of the invention, nucleic acid sequences encoding HPRM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries (Price (1993) Blood Rev 7:127–134; Trask (1991) Trends Genet 7:149–154).

Fluorescent in situ hybridization (FISH) may be correlated with other physical chromosome s mapping techniques and genetic map data (Heinz-Ulrich:et al. (1995) In: Meyers, *Molecular Biology and Biotechnology*, VCH Publishers New York N.Y., pp. 965–968). Examples of genetic map data can be found in various scientific journals or at the Online Mendelian Inheritance in Man (OMIM) site. Correlation between the location of the gene encoding BPRM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genonic region, e.g., AT to 11q22-23, any sequences mapping to that area may represent associated or regulatory genes for further investigation (Gatti et al. (1988) Nature 336:577–580). The nucleotide sequence of the subject invention may also be used to detect differences in the chromosomal location due to translocation, inversion, etc., among normal, carrier, or affected individuals.

In another embodiment of the invention, HPRM, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HPRM and the agent being tested may be measured.

Another technique for drug screening provides for high throughput screening of compounds having binding affinity to the protein of interest (Geysen, et al. (1984) PCT application WO84/03564). In this method, large numbers of different small test compounds are synthesized on a solid substrate, such as plastic pins or some other surface. The test compounds are reacted with HPRM, or fragments thereof, and washed. Bound HPRM is then detected by methods well known in the art. Purified HPRM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPRM specifically compete with a test compound for binding HPRM. In this manner, antibodies can be used to detect the presence of any peptide which shares one or more antigenic determinants with HPRM.

In additional embodiments, the nucleotide sequences which encode HPRM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I RATRNOT02 cDNA Library Construction

The right atrium tissue used for the RATRNOT02 library construction was obtained from a 39 year old Caucasian male who died of a gun shot wound. The frozen tissue was homogenized and lysed using a POLYTRON homogenizer (Brinkmann Instruments, Westbury N.Y.) in guanidinium isothiocyanate solution. The lysate was centrifuged over a 5.7 M CsCl cushion using an SW28 rotor in a L8-70M ultracentrifuge (Beckman Coulter, Fullerton Calif.) for 18 hours at 25,000 rpm at ambient temperature. The RNA was extracted with phenol chloroform, pH 4.0, precipitated using 0.3 M sodium acetate and 2.5 volumes of ethanol, resuspended in RNAse-free water and treated with DNase at 37° C. RNA extraction and precipitation were repeated as before. The mRNA was isolated with the OLIGOTEX kit (Qiagen, Valencia Calif.) and used to construct the cDNA library.

A 10 million clone cDNA library was constructed using three micrograms of poly $A^+$ mRNA and Not I/oligo d(T) primer. The cDNAs were directionally inserted into Sal I/Not I sites of PSPORT 1 plasmid (Life Technologies) and the plasmid was transformed into competent DH5($\alpha$ cells or ELECTROMAX DH10B cells (Life Technologies).

II Isolation and Sequencing of cDNA Clones

Plasmid DNA was released from the cells and purified using the MINIPREP kit (Advanced Genetic Technologies, Gaithersburg Md.). This kit consists of a 96-well block with reagents for 960 purifications. The recommended protocol was employed except for the following changes: 1) the 96 wells were each filled with 1 ml of sterile TERRIFIC BROTH (BD Biosciences, Sparks Md.) containing carbenicillin at 25 mg/l and glycerol at 0.4%; 2) the bacteria were inoculated into the wells, cultured for 24 hours, and then lysed with 60 $\mu$l of lysis buffer; 3) the blocks were centrifuged in the GS-6R rotor (Beckman Coulter) at 2900 rpm for 5 minutes, and the contents of the block were added to the primary filter plate; and 4) the optional step of adding isopropanol to TRIS buffer was eliminated. After the last step in the protocol, samples were transferred to a 96-well block for storage.

The cDNAs were prepared using a MICROLAB 2200 (Hamilton) in combination with DNA ENGINE thermal cyclers (MJ Research) and sequenced by the method of Sanger and Coulson (1975; J Mol Biol 94:441f) using 377 PRISM DNA sequencing systems (ABI); and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool; Altschul (1993) J Mol Evol 36:290–300; Altschul et al. (1990) J Mol Biol 215:403410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties (Smith et al. (1992) Protein Engineering 5:35–51). The sequences disclosed in this application have lengths of at least 49 nucleotides and have no more than 12% uncalled bases (where N is rpalces A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis program (Incyte Genomics, Palo Alto Calif.). This motif analysis program, based on sequence information contained in the SwissProt Database and PROSITE, is a method of determining the function of uncharacterized proteins translated from genomic or cDNA sequences (Bairoch et al. (1997) Nucleic Acids Res 25:217–221; Attwood et al. (1997) J Chem Inf Comput Sci 37:417–424). PROSITE may be used to identify common functional or structural domains in divergent proteins. The method is based on weight matrices. Motifs identified by this method are then calibrated against the SwissProt database in order to obtain a measure of the chance distribution of the matches.

In another alternative, Hidden Markov models (HMMs) may be used to find protein domains, each defined by a data set of proteins known to have a common biological function (Pearson and Lipman (1988) Proc Natl Acad Sci 85:2444–2448; Smith and Waterman (1981) J Mol Biol 147:195–197). HMMs were initially developed to examine speech recognition patterns, but are now being used in a biological context to analyze protein and nucleic acid sequences as well as to model protein structure (Keogh et al. (1994) J Mol Biol 235:1501–1531; Collin et al. (1993) Protein Sci 2:305–314). HMMs have a formal probabilistic basis and use position-specific scores for amino acids or nucleotides. The algorithm continues to incorporate information from newly identified sequences to increase its motif analysis capabilities.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook, supra, ch. 7; Ausubel, supra, ch. 4 and 16).

Analogous computer techniques applying BLAST are used to search for identical or related molecules in nucleotide databases such as GenBank or LIFESEQ database (Incyte Genomics). This analysis is much faster than multiple membrane-based hybridizations. In addition, the sensitivity of the computer search can be modified to determine whether any particular match is categorized as exact or homologous.

The basis of the search is the product score, which is defined as:

% sequence identity x% maximum BLAST score/100

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HPRM occurs. Abundance and percent abundance are also reported. Abundance directly reflects the number of times a particular transcript is represented in a cDNA library, and percent abundance is abundance divided by the total number of sequences examined in the cDNA library.

V Extension of HPRM Encoding Polynucleotides

The nucleic acid sequences of Incyte Clones 456855, 947429, and 1516165 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO software (Molecular Biology Insights), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (ABI) and thoroughly mixing the enzyme and reaction mix. PCR was performed using the DNA ENGINE thermal cycler (MJ Research), beginning with 40 pmol of each primer and the recommended concentrations of all other components of the kit, with the following parameters: Step 1, 94° C. for 1 min (initial denaturation); Step 2, 65° C. for 1 min; Step 3, 68° C. for 6 min; Step 4, 94° C. for 15 sec; Step 5, 65° C. for 1 min; Step 6, 68° C. for 7 min; Step 7, repeat steps 4 through 6 for an additional 15 cycles; Step 8, 94° C. for 15 sec; Step 9, 65° C. for 1 min; Step 10, 68° C. for 7: 15 min; Step 11, repeat steps 8 through 10 for an additional 12 cycles; Step 12, 72° C. for 8 min; and Step 13, 4° C. (and holding).

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (Qiagen), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium (Sambrook, supra, Appendix A, p. 2). After incubation for one hour at 37° C., the E. coli mixture was plated on Luria Bertani (LB) agar (Sambrook, supra, Appendix A, p. 1) containing carbenicillin (2×carb). The following day, several colonies were randomly picked from each plate and cultured in 150 μl of liquid LB/2×carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions: Step 1, 94° C. for 60 sec; Step 2, 94° C. for 20 sec; Step 3, 55° C. for 30 sec; Step 4, 72° C. for 90 sec; Step 5, repeat steps 2 through 4 for an additional 29 cycles; Step 6, 72° C. for 180 sec; and Step 7, 4° C. (and holding).

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NOs:4–6 are used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:4–6 are employed to screen cDNAs, genomic DNAs, or mRNAs. Although the labeling of oligonucleotides,: consisting of about 20 base pairs, is specifically described, essentially the same procedure is used with larger nucleotide fragments. Oligonucleotides are designed using state-of-the-art software such as OLIGO software (Molecular Biology Insights) and labeled by combining 50 pmol of each oligomer, 250 μCi of [γ-$^{32}$P] adenosine triphosphate (APB), and T4 polynucleotide kinase (PerkinElmer Life Sciences, Boston Mass.). The labeled oligonucleotides are purified using a SEPHADEX G-25 superfine resin column (APB). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (PerkinElmer Life Sciences).

The DNA from each digest is fractionated on a 0.7 percent agarose gel and transferred to NYTRAN PLUS membranes (Schleicher & Schuell, Keene N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak, Rochester N.Y.) is exposed to the blots for several hours, hybridization patterns are compared.

VII Microarrays

A chemical coupling procedure and an ink jet device can be used to synthesize array elements on the surface of a substrate (Baldeschweiler, supra). An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying (Schena et al. (1995) Science 270:467–470; Shalon et al. (1996) Genome Res 6:639–645). Fluorescent probes are prepared and used for hybridization to the elements on the substrate. The substrate is analyzed by procedures described above.

VIII Complementary Polynucleotides

Sequences complementary to the HPRM-encoding sequences, or any parts thereof, are used to detect, decrease, or inhibit expression of naturally occurring HPRM. Although use of oligonucleotides comprising from about 15 to 30 base pairs is described essentially the same procedure is used with smaller or with larger sequence fragments. Appropriate oligonucleotides are designed using OLIGO software (Molecular Biology Insights) and the coding sequence of HPRM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HPRM-encoding transcript.

IX Expression of HPRM

Expression of HPRM is accomplished by subcloning the cDNA into an appropriate vector and transforming the vector into host cells. This vector contains an appropriate promoter, e.g., β-galactosidase, upstream of the cloning site, operably associated with the cDNA of interest (Sambrook, supra, pp. 404–433; Rosenberg et al. (1983) Methods Enzymol 101:123–138).

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HPRM into bacterial growth media which can be used directly in the following assay for activity.

X Demonstration of HPRM Activity

Protease activity of HPRM is measured by the hydrolysis of appropriate synthetic peptide substrates conjugated with various chromogenic molecules in which the degree of hydrolysis is quantitated by spectrophotometric (or fluorometric) absorption of the released chromophore (Beynon and Bond, supra pp.25–55). Peptide substrates are designed according to the category of protease activity as endopeptidase (serine, cysteine, aspartic proteases), animopeptidase (leucine aminopeptidase), or carboxypeptidase (carboxypeptidase A and B, procollagen C-proteinase). Chromogens commonly used are 2-naphthylamine, 4-nitroaniline, and furylacrylic acid. Assays are performed at room temperature (~25° C.) and contain an aliquot of the enzyme and the appropriate substrate in a buffer. Reactions are carried out in an optical cuvette and followed by the increase/decrease in absorbance of the chromogen released during hydrolysis of the peptide substrate. The change in absorbance is proportional to the enzyme activity in the assay.

Enhancement of procollagen C-proteinase activity (HPRM-2) is determined by measuring procollagen C-proteinase activity in the absence and presence of enhancer protein. Procollagen C-proteinase activity is measured as described above using an appropriate carboxypeptidase substrate in the absence and in the presence of varying amounts of HPRM-2. The increase in activity of procollagen C-proteinase measured in the presence of HPRM-2 compared to that measured in its absence is proportional to the activity of HPRM-2 in the assay.

XI Production of HPRM Specific Antibodies

HPRM is purified using PAGE electrophoresis (Harrington(1990) Methods Enzymol 182:488–495), or other purification techniques, is used to immunize rabbits and to produce antibodies using standard protocols.

Alternatively, the HPRM amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art (Ausubel, supra, ch. 11).

Typically, oligopeptides 15 residues in length are synthesized using a Model 431A peptide synthesizer (ABI) using fmoc-chemistry and coupled to KLH (Sigma-Aldrich, St. Louis Mo.) by reaction with N-maleimidobenzoyl-N-hydroxysuccinimide ester (MBS) to increase immunogenicity (Ausubel, supra.). Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII Purification of Naturally Occurring HPRM Using Specific Antibodies

Naturally occurring or recombinant HPRM is purified by immunoaffinity chromatography using antibodies specific for HPRM. An immunoaffinity column is constructed by covalently coupling anti-HPRM antibody to an activated chromatographic resin, such as CNBr-activated SEPHAROSE resin (APB). After the coupling, the resin is blocked and washed according to the manufacturer's instructions.

Media containing HPRM are passed over the immunoaffinity column, and the column is washed under conditions, e.g., in high ionic strength buffers in the presence of detergent, that allow the preferential absorbance of HPRM. The column is eluted under conditions, e.g., a buffer of pH 2 to pH 3, or a high concentration of a chaotrope, such as urea or thiocyanate ion, that disrupt antibody/HPRM binding, and HPRM is collected.

XIII Identification of Molecules Which Interact with HPRM

HPRM, or biologically active fragments thereof, are labeled with $^{125}$I Bolton-Hunter reagent (Bolton et al. (1973) Biochem J 133:529–533). Candidate molecules previously arrayed in the wells of a multi-well plate are incubated with the labeled HPRM, washed, and any wells with labeled HPRM complex are assayed. Data obtained using different concentrations of HPRM are used to calculate values for the number, affinity, and association of HPRM with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising a protein having the amino acid sequence of SEQ ID NO:2 or a biologically active fragment of the protein comprising residue C34 to residue C415 of SEQ ID NO:2 wherein said biologically active fragment has protease activity.

2. A biologically active fragment of a protein consisting of residues C34–C415 of SEQ ID NO:2 wherein said biologically active fragment has protease activity.

3. A method for using a polypeptide to screen a plurality of molecules to identify a molecule which specifically binds the polypeptide, the method comprising:

a) combining the polypeptide of claim 1 with the plurality of molecules under conditions to allow specific binding; and b) detecting specific binding, thereby identifying a molecule which specifically binds the polypeptide.

4. A method of using a polypeptide to purify a molecule which specifically binds the polypeptide from a sample, the method comprising:

a) combining the polypeptide of claim 1 with a sample under conditions to allow specific binding;

b) recovering the bound polypeptide; and c) separating the molecule from the polypeptide, thereby obtaining the purified molecule.

5. A composition comprising the polypeptide of claim 1 and a pharmaceutical carrier.

6. A method for using a polypeptide to produce an antibody, the method comprising:

a) immunizing an animal with the polypeptide of claim 1 under conditions to elicit an antibody response; and b) isolating antibodies which bind specifically to the polypeptide.

7. A method for using a polypeptide to purify an antibody which specifically binds the polypeptide, the method comprising:

a) combining the polypeptide of claim 1 with a plurality of antibodies under conditions allow specific binding, b) recovering the bound polypeptide, and c) separating the antibody from the polypeptide, thereby obtaining antibody which specifically binds the polypeptide.

8. The method of claim 7, wherein the antibodies are selected from polyclonal antibodies, monoclonal antibodies, chimeric antibodies, single chain antibodies; Fab fragments, Fv fragments, and F(ab')$_2$ fragments.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 248 amino acids
        (B) TYPE: amino acid
        (C) STRANDEDNESS: single
        (D) TOPOLOGY: linear (vii) IMMEDIATE SOURCE:
        (A) LIBRARY: KERANOT01
        (B) CLONE: 456855

(xi) SEQUENCE DESCRIPTION: SEQ ID NO: 1:

Met Phe Leu Ala Lys Ala Leu Leu Glu Gly Ala Asp Arg Gly Leu Gly
1               5                   10                  15

Glu Ala Leu Gly Gly Leu Phe Gly Gly Gly Gln Arg Arg Glu Gly
                20                  25                  30

Gly Gly Arg Asn Ile Gly Gly Ile Val Gly Gly Ile Val Asn Phe Ile
                35                  40                  45

Ser Glu Ala Ala Ala Ala Gln Tyr Thr Pro Glu Pro Pro Thr Gln
    50                  55                  60

Gln His Phe Thr Ser Val Glu Ala Ser Glu Ser Glu Val Arg Arg
65              70                  75                  80

Phe Arg Gln Gln Phe Thr Gln Leu Ala Gly Pro Asp Met Glu Val Gly
                85                  90                  95

Ala Thr Asp Leu Met Asn Ile Leu Asn Lys Val Leu Ser Lys His Lys
                100                 105                 110

Asp Leu Lys Thr Asp Gly Phe Ser Leu Asp Thr Cys Arg Ser Ile Val
                115                 120                 125

Ser Val Met Asp Ser Asp Thr Thr Gly Lys Leu Gly Phe Glu Glu Phe
    130                 135                 140

Lys Tyr Leu Trp Asn Asn Ile Lys Lys Trp Gln Cys Val Tyr Lys Gln
145                 150                 155                 160

Tyr Asp Arg Asp His Ser Gly Ser Leu Gly Ser Ser Gln Leu Arg Gly
                165                 170                 175

Ala Leu Gln Ala Ala Gly Phe Gln Leu Asn Glu Gln Leu Tyr Gln Met
                180                 185                 190

Ile Val Arg Arg Tyr Ala Asn Glu Asp Gly Asp Met Asp Phe Asn Asn
                195                 200                 205

Phe Ile Ser Cys Leu Val Arg Leu Asp Ala Met Phe Arg Ala Phe Lys
    210                 215                 220

Ser Leu Asp Arg Asp Arg Asp Gly Leu Ile Gln Val Ser Ile Lys Glu
225                 230                 235                 240

Trp Leu Gln Leu Thr Met Tyr Ser
                245

(2) INFORMATION FOR SEQ ID NO: 2:

(i) SEQUENCE CHARACTERISTICS:
        (A) LENGTH: 415 amino acids
        (B) TYPE: amino acid
        (C) STRANDEDNESS: single
        (D) TOPOLOGY: linear (vii) IMMEDIATE SOURCE:
        (A) LIBRARY: RATRNOT02
        (B) CLONE: 947429

(xi) SEQUENCE DESCRIPTION: SEQ ID NO: 2:

Met Arg Gly Ala Asn Ala Trp Ala Pro Leu Cys Leu Leu Ala Ala
1               5                   10                  15

Ala Thr Gln Leu Ser Arg Gln Gln Ser Pro Glu Arg Pro Val Phe Thr

```
                    20                  25                  30
Cys Gly Gly Ile Leu Thr Gly Glu Ser Gly Phe Ile Gly Ser Glu Gly
                35                  40                  45

Phe Pro Gly Val Tyr Pro Pro Asn Ser Lys Cys Thr Trp Lys Ile Thr
     50                  55                  60

Val Pro Glu Gly Lys Val Val Leu Asn Phe Arg Phe Ile Asp Leu
65                   70                  75                  80

Glu Ser Asp Asn Leu Cys Arg Tyr Asp Phe Val Asp Val Tyr Asn Gly
                85                  90                  95

His Ala Asn Gly Gln Arg Ile Gly Arg Phe Cys Gly Thr Phe Arg Pro
                100                 105                 110

Gly Ala Leu Val Ser Ser Gly Asn Lys Met Met Val Gln Met Ile Phe
            115                 120                 125

Asp Ala Asn Thr Ala Gly Asn Gly Phe Met Ala Met Phe Ser Ala Ala
        130                 135                 140

Glu Pro Asn Glu Arg Gly Asp Gln Tyr Cys Gly Gly Leu Leu Asp Arg
145                 150                 155                 160

Pro Ser Gly Ser Phe Lys Thr Pro Asn Trp Pro Asp Arg Asp Tyr Pro
                165                 170                 175

Ala Gly Val Thr Cys Val Trp His Ile Val Ala Pro Lys Asn Gln Leu
            180                 185                 190

Ile Glu Leu Lys Phe Glu Lys Phe Asp Val Glu Arg Asp Asn Tyr Cys
        195                 200                 205

Arg Tyr Asp Tyr Val Ala Val Phe Asn Gly Gly Glu Val Asn Asp Ala
    210                 215                 220

Arg Arg Ile Gly Lys Tyr Cys Gly Asp Ser Pro Pro Ala Pro Ile Val
225                 230                 235                 240

Ser Glu Arg Asn Glu Leu Leu Ile Gln Phe Leu Ser Asp Leu Ser Leu
                245                 250                 255

Thr Ala Asp Gly Phe Ile Gly His Tyr Ile Phe Arg Pro Lys Lys Leu
            260                 265                 270

Pro Thr Thr Thr Glu Gln Pro Val Thr Thr Thr Phe Pro Val Thr Thr
        275                 280                 285

Gly Leu Lys Pro Thr Val Ala Leu Cys Gln Gln Lys Cys Arg Arg Thr
    290                 295                 300

Gly Thr Leu Glu Gly Asn Tyr Cys Ser Ser Asp Phe Val Leu Ala Gly
305                 310                 315                 320

Thr Val Ile Thr Thr Ile Thr Arg Asp Gly Ser Leu His Ala Thr Val
                325                 330                 335

Ser Ile Ile Asn Ile Tyr Lys Glu Gly Asn Leu Ala Ile Gln Gln Ala
            340                 345                 350

Gly Lys Asn Met Ser Ala Arg Leu Thr Val Val Cys Lys Gln Cys Pro
        355                 360                 365

Leu Leu Arg Arg Gly Leu Asn Tyr Ile Ile Met Gly Gln Val Gly Glu
    370                 375                 380

Asp Gly Arg Gly Lys Ile Met Pro Asn Ser Phe Ile Met Met Phe Lys
385                 390                 395                 400

Thr Lys Asn Gln Lys Leu Leu Asp Ala Leu Lys Asn Lys Gln Cys
                405                 410                 415

(2) INFORMATION FOR SEQ ID NO: 3:

(i) SEQUENCE CHARACTERISTICS:
        (A) LENGTH: 349 amino acids
```

(B) TYPE: amino acid
(C) STRANDEDNESS: single
(D) TOPOLOGY: linear (vii) IMMEDIATE SOURCE:
(A) LIBRARY: PANCTUT01
(B) CLONE: 1515165

(xi) SEQUENCE DESCRIPTION: SEQ ID NO: 3:

```
Met Lys Thr Leu Leu Leu Leu Val Leu Glu Leu Gly Glu
 1               5                  10              15

Ala Gln Gly Ser Leu His Arg Val Pro Leu Arg Arg His Pro Ser Leu
            20                  25                  30

Lys Lys Lys Leu Arg Ala Arg Ser Gln Leu Ser Glu Phe Trp Lys Ser
            35                  40                  45

His Asn Leu Asp Met Ile Gln Phe Thr Glu Ser Cys Ser Met Asp Gln
 50                  55                  60

Ser Ala Lys Glu Pro Leu Ile Asn Tyr Leu Asp Met Glu Tyr Phe Gly
 65                  70                  75                  80

Thr Ile Ser Ile Gly Ser Pro Pro Gln Asn Phe Thr Val Ile Phe Asp
                85                  90                  95

Thr Gly Ser Ser Asn Leu Trp Val Pro Ser Val Tyr Cys Thr Ser Pro
                100                 105                 110

Ala Cys Lys Thr His Ser Arg Phe Gln Pro Ser Gln Ser Ser Thr Tyr
                115                 120                 125

Ser Gln Pro Gly Gln Ser Phe Ser Ile Gln Tyr Gly Thr Gly Ser Leu
            130                 135                 140

Ser Gly Ile Ile Gly Ala Asp Gln Val Ser Val Glu Gly Leu Thr Val
145                 150                 155                 160

Val Gly Gln Gln Phe Gly Glu Ser Val Thr Glu Pro Gly Gln Thr Phe
                165                 170                 175

Val Asp Ala Glu Phe Asp Gly Ile Leu Gly Leu Gly Tyr Pro Ser Leu
                180                 185                 190

Ala Val Gly Gly Val Thr Pro Val Phe Asp Asn Met Met Ala Gln Asn
            195                 200                 205

Leu Val Asp Leu Pro Met Phe Ser Val Tyr Met Ser Ser Asn Pro Glu
210                 215                 220

Gly Gly Ala Gly Ser Glu Leu Ile Phe Gly Gly Tyr Asp His Ser His
225                 230                 235                 240

Phe Ser Gly Ser Leu Asn Trp Val Pro Val Thr Lys Gln Ala Tyr Trp
                245                 250                 255

Gln Ile Ala Leu Asp Asn Tyr Ala Val Glu Cys Ala Asn Leu Asn Val
            260                 265                 270

Met Pro Asp Val Thr Phe Thr Ile Asn Gly Val Pro Tyr Thr Leu Ser
            275                 280                 285

Pro Thr Ala Tyr Thr Leu Leu Asp Phe Val Asp Gly Met Gln Phe Cys
        290                 295                 300

Ser Ser Gly Phe Gln Gly Leu Asp Ile His Pro Pro Ala Gly Pro Leu
305                 310                 315                 320

Trp Ile Leu Gly Asp Val Phe Ile Arg Gln Phe Tyr Ser Val Phe Asp
                325                 330                 335

Arg Gly Asn Asn Arg Val Gly Leu Ala Pro Ala Val Pro
                340                 345
```

(2) INFORMATION FOR SEQ ID NO: 4:

```
    (i) SEQUENCE CHARACTERISTICS:
        (A) LENGTH: 1000 base pairs
        (B) TYPE: nucleic acid
        (C) STRANDEDNESS: single
        (D) TOPOLOGY: linear (vii) IMMEDIATE SOURCE:
        (A) LIBRARY: KERANOT01
        (B) CLONE: 456855

(xi) SEQUENCE DESCRIPTION: SEQ ID NO: 4:

TTTTTTCATA CCATCTCTAA GATTGCTGCC GCATTTGCTT GTTAAACTGA AAGCATGTTT      60

CTTGCAAAGG CTCTATTGGA AGGAGCAGAT CGAGGTCTTG GAGAAGCTCT TGGAGGCCTC     120

TTTGGAGGAG GTGGTCAGAG AAGAGAAGGA GGAGGAAGAA ATATTGGAGG GATAGTTGGA     180

GGAATTGTGA ATTTTATCAG TGAGGCTGCA GCAGCTCAGT ATACTCCAGA ACCGCCTCCC     240

ACTCAGCAGC ATTTCACCAG TGTGGAGGCC TCAGAAAGTG AGGAAGTTAG GCGATTTCGG     300

CAACAATTTA CACAGCTGGC TGGACCAGAC ATGGAGGTGG GTGCCACTGA TCTGATGAAT     360

ATTCTCAACA AAGTCCTTTC TAAGCACAAA GATCTTAAGA CTGACGGTTT TAGTCTTGAC     420

ACCTGCCGGA GCATTGTGTC TGTCATGGAC AGTGACACGA CTGGTAAGCT GGGCTTTGAA     480

GAATTTAAGT ATCTGTGGAA CAACATCAAG AAATGGCAGT GTGTTTATAA GCAGTATGAC     540

AGGGACCATT CTGGGTCTCT GGGAAGTTCT CAGCTGCGGG GAGCTCTGCA GGCCGCAGGC     600

TTCCAGCTAA ATGAACAACT TTACCAAATG ATTGTCCGCC GGTATGCTAA TGAAGATGGA     660

GATATGGATT TTAACAATTT CATCAGCTGC TTGGTCCGCC TGGATGCCAT GTTTCGTGCC     720

TTCAAGTCTC TGGATAGAGA TAGAGATGGC CTGATTCAAG TGTCTATCAA AGAGTGGCTG     780

CAGTTGACCA TGTATTCCTG AAGTGGGAAC TGAGAAGTCA AGATCCTCCC TGGAGGACAG     840

GACTGAAAAC CTTGCCAAGC TGTACACAGT TGCTGATACC CTGTGCAACA GCTCTCATTT     900

CCTGGCAAGC TCTTTCACAA CCCTACATAT TTCTGATCAT GTGCTGCCTT TTACTGCTGA     960

ATTAAAACAG ATATTTCACG AAAAAAAAAA AAAAAAAAA                          1000

(2) INFORMATION FOR SEQ ID NO: 5:

(i) SEQUENCE CHARACTERISTICS:
        (A) LENGTH: 1802 base pairs
        (B) TYPE: nucleic acid
        (C) STRANDEDNESS: single
        (D) TOPOLOGY: linear (xi) SEQUENCE DESCRIPTION: SEQ ID NO: 5:

CGCTGTCGGT GCGGCGGCGC GCGTGCGGGT GCAAACCCGA GCGTCTACGC TGCCATGAGG      60

GGCGCGAACG CCTGGGCGCC ACTCTGCCTG CTGCTGGCTG CCGCCACCCA GCTCTCGCGG     120

CAGCAGTCCC CAGAGAGACC TGTTTTCACA TGTGGTGGCA TTCTTACTGG AGAGTCTGGA     180

TTTATTGGCA GTGAAGGTTT TCCTGGAGTG TACCCTCCAA ATAGCAAATG TACTTGGAAA     240

ATCACAGTTC CCGAAGGAAA AGTAGTCGTT CTCAATTTCC GATTCATAGA CCTCGAGAGT     300

GACAACCTGT GCCGCTATGA CTTTGTGGAT GTGTACAATG GCCATGCCAA TGGCCAGCGC     360

ATTGGCCGCT TCTGTGGCAC TTTCCGGCCT GGAGCCCTTG TGTCCAGTGG CAACAAGATG     420

ATGGTGCAGA TGATTTTTGA TGCCAACACA GCTGGCAATG GCTTCATGGC CATGTTCTCC     480

GCTGCTGAAC CAAACGAAAG AGGGGATCAG TATTGTGGAG GACTCCTTGA CAGACCTTCC     540

GGCTCTTTTA AAACCCCCAA CTGGCCAGAC CGGGATTACC CTGCAGGAGT CACTTGTGTG     600

TGGCACATTG TAGCCCCAAA GAATCAGCTT ATAGAATTAA AGTTTGAGAA GTTTGATGTG     660
```

-continued

```
GAGCGAGATA ACTACTGCCG ATATGATTAT GTGGCTGTGT TTAATGGCGG GGAAGTCAAC        720

GATGCTAGAA GAATTGGAAA GTATTGTGGT GATAGTCCAC CTGCGCCAAT TGTGTCTGAG        780

AGAAATGAAC TTCTTATTCA GTTTTTATCA GACTTAAGTT TAACTGCAGA TGGGTTTATT        840

GGTCACTACA TATTCAGGCC AAAAAAACTG CCTACAACTA CAGAACAGCC TGTCACCACC        900

ACATTCCCTG TAACCACGGG TTTAAAACCC ACCGTGGCCT TGTGTCAACA AAAGTGTAGA        960

CGGACGGGGA CTCTGGAGGG CAATTATTGT TCAAGTGACT TTGTATTAGC CGGCACTGTT       1020

ATCACAACCA TCACTCGCGA TGGGAGTTTG CACGCCACAG TCTCGATCAT CAACATCTAC       1080

AAAGAGGGAA ATTTGGCGAT TCAGCAGGCG GGCAAGAACA TGAGTGCCAG GCTGACTGTC       1140

GTCTGCAAGC AGTGCCCTCT CCTCAGAAGA GGTCTAAATT ACATTATTAT GGGCCAAGTA       1200

GGTGAAGATG GGCGAGGCAA AATCATGCCA AACAGCTTTA TCATGATGTT CAAGACCAAG       1260

AATCAGAAGC TCCTGGATGC CTTAAAAAAT AAGCAATGTT AACAGTGAAC TGTGTCCATT       1320

TAAGCTGTAT TCTGCCATTG CCTTTGAAAG ATCTATGTTC TCTCAGTAGA AAAAAAAATA       1380

CTTATAAAAT TACATATTCT GAAAGAGGAT TCCGAAAGAT GGGACTGGTT GACTCTTCAC       1440

ATGATGGAGG TATGAGGCCT CCGAGATAGC TGAGGGAAGT TCTTTGCCTG CTGTCAGAGG       1500

AGCAGCTATC TGATTGGAAA CCTGCCGACT TAGTGCGGTG ATAGGAAGCT AAAAGTGTCA       1560

AGCGTTGACA GCTTGGAAGC GTTTATTTAT ACATCTCTGT AAAAGGATAT TTTAGAATTG       1620

AGTTGTGTGA AGATGTCAAA AAAGATTTT AGAAGTGCAA TATTTATAGT GTTATTTGTT       1680

TCACCTTCAA GCCTTTGCCC TGAGGTGTTA CAATCTTGTC TTGCGTTTTC TAAATCAATG       1740

CTTAATAAAA TATTTTTAAA GGAAAAAAAA AAAAAAAAA AAAAAAAAAA AAAAAACGA       1800

AT                                                                    1802

(2) INFORMATION FOR SEQ ID NO: 6:

(i) SEQUENCE CHARACTERISTICS:
        (A) LENGTH: 2073 base pairs
        (B) TYPE: nucleic acid
        (C) STRANDEDNESS: single
        (D) TOPOLOGY: linear (vii) IMMEDIATE SOURCE:
        (A) LIBRARY: PANCTUT01
        (B) CLONE: 1515165

(xi) SEQUENCE DESCRIPTION: SEQ ID NO: 6:

CGGAGGGGGC AAGGGAGAAG CTGCTGGTCG GACTCACAAT GAAAACGCTC CTTCTTTTGC         60

TGCTGGTGCT CCTGGAGCTG GGAGAGGCCC AAGGATCCCT TCACAGGGTG CCCCTCAGGA        120

GGCATCCGTC CCTCAAGAAG AAGCTGCGGG CACGGAGCCA GCTCTCTGAG TTCTGGAAAT        180

CCCATAATTT GGACATGATC CAGTTCACCG AGTCCTGCTC AATGGACCAG AGTGCCAAGG        240

AACCCCTCAT CAACTACTTG GATATGGAAT ACTTCGGCAC TATCTCCATT GGCTCCCCAC        300

CACAGAACTT CACTGTCATC TTCGACACTG GCTCCTCCAA CCTCTGGGTC CCCTCTGTGT        360

ACTGCACTAG CCCAGCCTGC AAGACGCACA GCAGGTTCCA GCCTTCCCAG TCCAGCACAT        420

ACAGCCAGCC AGGTCAATCT TTCTCCATTC AGTATGGAAC CGGGAGCTTG TCCGGGATCA        480

TTGGAGCCGA CCAAGTCTCT GTGGAAGGAC TAACCGTGGT TGGCCAGCAG TTTGAGAAAA        540

GTGTCACAGA GCCAGGCCAG ACCTTTGTGG ATGCAGAGTT TGATGGAATT CTGGGCCTGG        600

GATACCCCTC CTTGGCTGTG GGAGGAGTGA CTCCAGTATT TGACAACATG ATGGCTCAGA        660

ACCTGGTGGA CTTGCCGATG TTTTCTGTCT ACATGAGCAG TAACCCAGAA GGTGGTGCCG        720
```

```
GGAGCGAGCT GATTTTTGGA GGCTACGACC ACTCCCATTT CTCTGGGAGC CTGAATTGGG      780

TCCCAGTCAC CAAGCAAGCT TACTGGCAGA TTGCACTGGA TAACTATGCT GTGGAGTGTG      840

CCAACCTTAA CGTCATGCCG GATGTCACCT TCACCATTAA CGGAGTCCCC TATACCCTCA      900

GCCCAACTGC CTACACCCTA CTGGACTTCG TGGATGGAAT GCAGTTCTGC AGCAGTGGCT      960

TTCAAGGACT TGACATCCAC CCTCCAGCTG GGCCCTCTG GATCCTGGGG GATGTCTTCA      1020

TTCGACAGTT TTACTCAGTC TTTGACCGTG GAATAACCG TGTGGGACTG GCCCCAGCAG      1080

TCCCCTAAGG AGGGGCCTTG TGTCTGTGCC TGCCTGTCTG ACAGACCTTG AATATGTTAG      1140

GCTGGGGCAT TCTTTACACC TACAAAAAGT TATTTTCCAG AGAATGTAGC TGTTTCCAGG      1200

GTTGCAACTT GAATTAAGAC CAAACAGAAC ATGAGAATAC ACACACACAC ACACATATAC      1260

ACACACACAC ACTTCACACA TACACACCAC TCCCACCACC GTCATGATGG AGGAATTACG      1320

TTATACATTC ATATTTTGTA TTGATTTTTG ATTATGAAAA TCAAAAATTT TCACATTTGA      1380

TTATGAAAAT CTCCAAACAT ATGCACAAGC AGAGATCATG GTATAATAAA TCCCTTTGCA      1440

ACTCCACTCA GCCCTGACAA CCCATCCACA CACGGCCAGG CCTGTTTATC TACACTGCTG      1500

CCCACTCCTC TCTCCAGCTC CACATGCTGT ACCTGGATCA TTCTGAAGCA AATTCCGAGC      1560

ATTACATCAT TTTGTCCATA AATATTTCTA ACATCCTTAA ATATACAATC GGAATTCAAG      1620

CATCTCCCAT TGTCCCACAA ATGTTTGGCT GTTTTTGTAG TTGGATTGTT TGTATTAGGA      1680

TTCAAGCAAG GCCCATATAT TGCATTTATT TGAAATGTCT GTAAGTCTCT TTCCATCTAC      1740

AGAGTTTAGC ACATTTGAAC GTTGCTGGTT GAAATCCCGA GGTGTCATTT GACATGGTTC      1800

TCTGAACTTA TCTTTCCTAT AAAATGGTAG TTAGATCTGG AGGTCTGATT TTGTGGCAAA      1860

AATACTTCCT AGGTGGTGCT GGGTACTTCT TGTTGCATCC TGTCAGGAGG CAGATAATGC      1920

TGGTGCCTCT CTATTGGTAA TGTTAAGACT GCTGGGTGGG TTTGGAGTTC TTGGCTTTAA      1980

TCATTCATTA CAAAGTTCAG CATTTTAAAA AAAAAAAAA AAAAGGAAAA AAGAAAGAAA      2040

AAGAGAAAAA AGAAAAAAAA AAGGAAAGAG GGG                                   2073
```

(2) INFORMATION FOR SEQ ID NO: 7:

(i) SEQUENCE CHARACTERISTICS:
        (A) LENGTH: 266 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 164403

(xi) SEQUENCE DESCRIPTION: SEQ ID NO: 7:

```
Met Phe Leu Val Asn Ser Phe Leu Lys Gly Gly Gly Gly Gly Gly
 1               5                  10                  15

Gly Gly Gly Gly Leu Gly Gly Gly Leu Gly Asn Val Leu Gly Gly Leu
            20                  25                  30

Ile Ser Gly Ala Gly Gly Gly Gly Gly Gly Gly Gly Gly Gly
            35                  40                  45

Gly Gly Gly Gly Gly Gly Thr Ala Met Arg Ile Leu Gly Gly Val Ile
        50                  55                  60

Ser Ala Ile Ser Glu Ala Ala Ala Gln Tyr Asn Pro Glu Pro Pro
65                  70                  75                  80

Pro Arg Thr His Tyr Ser Asn Ile Glu Ala Asn Glu Ser Glu Glu Val
                85                  90                  95
```

-continued

```
Arg Gln Phe Arg Arg Leu Phe Ala Gln Leu Ala Gly Asp Asp Met Glu
                100                 105                 110

Val Ser Ala Thr Glu Leu Met Asn Ile Leu Asn Lys Val Val Thr Arg
            115                 120                 125

His Pro Asp Leu Lys Thr Asp Gly Phe Gly Ile Asp Thr Cys Arg Ser
        130                 135                 140

Met Val Ala Val Met Asp Ser Asp Thr Thr Gly Lys Leu Gly Phe Glu
145                 150                 155                 160

Glu Phe Lys Tyr Leu Trp Asn Asn Ile Lys Lys Trp Gln Ala Ile Tyr
                165                 170                 175

Lys Gln Phe Asp Val Asp Arg Ser Gly Thr Ile Gly Ser Ser Glu Leu
            180                 185                 190

Pro Gly Ala Phe Glu Ala Ala Gly Phe His Leu Asn Glu His Leu Tyr
        195                 200                 205

Ser Met Ile Ile Arg Arg Tyr Ser Asp Glu Gly Gly Asn Met Asp Phe
210                 215                 220

Asp Asn Phe Ile Ser Cys Leu Val Arg Leu Asp Ala Met Phe Arg Ala
225                 230                 235                 240

Phe Lys Ser Leu Asp Lys Asp Gly Thr Gly Gln Ile Gln Val Asn Ile
                245                 250                 255

Gln Glu Trp Leu Gln Leu Thr Met Tyr Ser
            260                 265
```

(2) INFORMATION FOR SEQ ID NO: 8:

(i) SEQUENCE CHARACTERISTICS:
        (A) LENGTH: 468 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2589009

(xi) SEQUENCE DESCRIPTION: SEQ ID NO: 8:

```
Met Leu Pro Ala Ala Leu Thr Ser Phe Leu Gly Pro Phe Leu Leu Ala
1               5                   10                  15

Trp Val Leu Pro Leu Ala Arg Gly Gln Thr Pro Asn Tyr Thr Arg Pro
                20                  25                  30

Val Phe Leu Cys Gly Gly Asp Val Thr Gly Glu Ser Gly Tyr Val Ala
            35                  40                  45

Ser Glu Gly Phe Pro Asn Leu Tyr Pro Pro Asn Lys Lys Cys Ile Trp
        50                  55                  60

Thr Ile Thr Val Pro Glu Gly Gln Thr Val Ser Leu Ser Phe Arg Val
65                  70                  75                  80

Phe Asp Met Glu Leu His Pro Ser Cys Arg Tyr Asp Ala Leu Glu Val
                85                  90                  95

Phe Ala Gly Ser Gly Thr Ser Gly Gln Arg Leu Gly Arg Phe Cys Gly
            100                 105                 110

Thr Phe Arg Pro Ala Pro Val Val Ala Pro Gly Asn Gln Val Thr Leu
        115                 120                 125

Arg Met Thr Thr Asp Glu Gly Thr Gly Gly Arg Gly Phe Leu Leu Trp
130                 135                 140

Tyr Ser Gly Arg Ala Thr Ser Gly Thr Glu His Gln Phe Cys Gly Gly
                145                 150                 155                 160
```

```
Arg Met Glu Lys Ala Gln Gly Thr Leu Thr Thr Pro Asn Trp Pro Glu
                165                 170                 175

Ser Asp Tyr Pro Pro Gly Ile Ser Cys Ser Trp His Ile Ile Ala Pro
            180                 185                 190

Ser Asn Gln Val Ile Met Leu Thr Phe Gly Lys Phe Asp Val Glu Pro
        195                 200                 205

Asp Thr Tyr Cys Arg Tyr Asp Ser Val Ser Val Phe Asn Gly Ala Val
    210                 215                 220

Ser Asp Asp Ser Lys Arg Leu Gly Lys Phe Cys Gly Asp Lys Ala Pro
225                 230                 235                 240

Ser Pro Ile Ser Ser Glu Gly Asn Glu Leu Leu Val Gln Phe Val Ser
            245                 250                 255

Asp Leu Ser Val Thr Ala Asp Gly Phe Ser Ala Ser Tyr Arg Thr Leu
        260                 265                 270

Pro Arg Asp Ala Val Glu Lys Glu Ser Ala Leu Ser Pro Gly Glu Asp
    275                 280                 285

Val Gln Arg Gly Pro Gln Ser Arg Ser Asp Pro Lys Thr Gly Thr Gly
290                 295                 300

Pro Lys Val Lys Pro Pro Thr Lys Pro Lys Ser Gln Pro Ala Glu Thr
305                 310                 315                 320

Pro Glu Ala Ser Pro Ala Thr Gln Ala Thr Pro Val Ala Pro Ala Ala
            325                 330                 335

Pro Ser Ile Thr Cys Pro Lys Gln Tyr Lys Arg Ser Gly Thr Leu Gln
            340                 345                 350

Ser Asn Phe Cys Ser Ser Ser Leu Val Val Thr Gly Thr Val Lys Thr
        355                 360                 365

Met Val Arg Gly Pro Gly Glu Gly Leu Thr Val Thr Val Ser Leu Leu
        370                 375                 380

Gly Val Tyr Lys Thr Gly Gly Leu Asp Leu Pro Ser Pro Pro Ser Gly
385                 390                 395                 400

Thr Ser Leu Lys Leu Tyr Val Pro Cys Arg Gln Met Pro Pro Met Lys
                405                 410                 415

Lys Gly Ala Ser Tyr Leu Leu Met Gly Gln Val Glu Glu Asn Arg Gly
                420                 425                 430

Pro Ile Leu Pro Pro Glu Ser Phe Val Val Leu Tyr Arg Ser Asn Gln
                435                 440                 445

Asp Gln Ile Leu Asn Asn Leu Ser Lys Arg Lys Cys Pro Ser Gln Pro
    450                 455                 460

Arg Thr Ala Ala
465

(2) INFORMATION FOR SEQ ID NO: 9:

(i) SEQUENCE CHARACTERISTICS:
        (A) LENGTH: 396 amino acids
        (B) TYPE: amino acid
        (C) STRANDEDNESS: single
        (D) TOPOLOGY: linear (vii) IMMEDIATE SOURCE:
        (A) LIBRARY: Genbank
        (B) CLONE: 181994
```

(xi) SEQUENCE DESCRIPTION: SEQ ID NO: 9:

```
Met Lys Thr Leu Leu Leu Leu Val Leu Glu Leu Gly Glu
 1               5                  10                  15
Ala Gln Gly Ser Leu His Arg Val Pro Leu Arg Arg His Pro Ser Leu
             20                  25                  30
Lys Lys Lys Leu Arg Ala Arg Ser Gln Leu Ser Glu Phe Trp Lys Ser
         35                  40                  45
His Asn Leu Asp Met Ile Gln Phe Thr Glu Ser Cys Ser Met Asp Gln
     50                  55                  60
Ser Ala Lys Glu Pro Leu Ile Asn Tyr Leu Asp Met Glu Tyr Phe Gly
 65                  70                  75                  80
Thr Ile Ser Ile Gly Ser Pro Pro Gln Asn Phe Thr Val Ile Phe Asp
                 85                  90                  95
Thr Gly Ser Ser Asn Leu Trp Val Pro Ser Val Tyr Cys Thr Ser Pro
            100                 105                 110
Ala Cys Lys Thr His Ser Arg Phe Gln Pro Ser Gln Ser Ser Thr Tyr
        115                 120                 125
Ser Gln Pro Gly Gln Ser Phe Ser Ile Gln Tyr Gly Thr Gly Ser Leu
    130                 135                 140
Ser Gly Ile Ile Gly Ala Asp Gln Val Ser Val Glu Gly Leu Thr Val
145                 150                 155                 160
Val Gly Gln Gln Phe Gly Glu Ser Val Thr Glu Pro Gly Gln Thr Phe
                165                 170                 175
Val Asp Ala Glu Phe Asp Gly Ile Leu Gly Leu Gly Tyr Pro Ser Leu
            180                 185                 190
Ala Val Gly Gly Val Thr Pro Val Phe Asp Asn Met Met Ala Gln Asn
        195                 200                 205
Leu Val Asp Leu Pro Met Phe Ser Val Tyr Met Ser Ser Asn Pro Glu
    210                 215                 220
Gly Gly Ala Gly Ser Glu Leu Ile Phe Gly Gly Tyr Asp His Ser His
225                 230                 235                 240
Phe Ser Gly Ser Leu Asn Trp Val Pro Val Thr Lys Gln Ala Tyr Trp
                245                 250                 255
Gln Ile Ala Leu Asp Asn Ile Gln Val Gly Gly Thr Val Met Phe Cys
            260                 265                 270
Ser Glu Gly Cys Gln Ala Ile Val Asp Thr Gly Thr Ser Leu Ile Thr
        275                 280                 285
Gly Pro Ser Asp Lys Ile Lys Gln Leu Gln Asn Ala Ile Gly Ala Ala
    290                 295                 300
Pro Val Asp Gly Glu Tyr Ala Val Glu Cys Ala Asn Leu Asn Val Met
305                 310                 315                 320
Pro Asp Val Thr Phe Thr Ile Asn Gly Val Pro Tyr Thr Leu Ser Pro
                325                 330                 335
Thr Ala Tyr Thr Leu Leu Asp Phe Val Asp Gly Met Gln Phe Cys Ser
            340                 345                 350
Ser Gly Phe Gln Gly Leu Asp Ile His Pro Pro Ala Gly Pro Leu Trp
        355                 360                 365
Ile Leu Gly Asp Val Phe Ile Arg Gln Phe Tyr Ser Val Phe Asp Arg
    370                 375                 380
Gly Asn Asn Arg Val Gly Leu Ala Pro Ala Val Pro
385                 390                 395
```